(12) United States Patent
Mehrpouyan et al.

(10) Patent No.: US 9,523,679 B2
(45) Date of Patent: *Dec. 20, 2016

(54) CHROMOPHORE COMPOSITIONS AND METHODS OF MAKING AND USING THE SAME

(71) Applicant: Becton, Dickinson and Company, Franklin Lakes, NJ (US)

(72) Inventors: Majid Mehrpouyan, Gilroy, CA (US); Oleg Guryev, Livermore, CA (US); Marybeth Sharkey, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 35 days.

This patent is subject to a terminal disclaimer.

(21) Appl. No.: 14/755,763

(22) Filed: Jun. 30, 2015

(65) Prior Publication Data

US 2015/0362484 A1 Dec. 17, 2015

Related U.S. Application Data

(63) Continuation of application No. 14/177,134, filed on Feb. 10, 2014, now Pat. No. 9,110,070.

(60) Provisional application No. 61/763,097, filed on Feb. 11, 2013.

(51) Int. Cl.
  *G01N 33/58* (2006.01)
  *G01N 33/53* (2006.01)
  *G01N 21/64* (2006.01)

(52) U.S. Cl.
  CPC ...... *G01N 33/5306* (2013.01); *G01N 21/6428* (2013.01); *G01N 33/582* (2013.01); *G01N 2021/6439* (2013.01); *G01N 2333/805* (2013.01)

(58) Field of Classification Search
  CPC .................................................. G01N 33/582
  See application file for complete search history.

(56) References Cited

U.S. PATENT DOCUMENTS 7,803,912 B2    9/2010  Olson et al.
9,110,070 B2 *  8/2015  Mehrpouyan ........ G01N 33/582

OTHER PUBLICATIONS

Bose et al., "Comparison of the Dielectric Response Obtained from Fluorescence Upconversion Measurements and Molecular Dynamics Simulations for Coumarin 153-Apomyoglobin Complexes and Structural Analysis of the Complexes by NMR and Fluorescence Methods", The Journal of Physical Chemistry A, vol. 115, No. 16, pp. 3630-3641 (2011).
Chowdhury et al. "The complex of apomyoglobin with the fluorescent dye coumar in 153'," Photochemistry and Photobiology, vol. 79, No. 5, pp. 440-446 (2004).
Dsouza et al., "Fluorescent Dyes and Their Supramolecular Host/Guest Complexes with Macrocycles in Aqueous Solution", Chemical Reviews, vol. 111, No. 12, pp. 7941-7980 (2011).
Luo et al., "Ultrafast Relaxation of Zinc Protoporphyrin Encapsulated within Apomyoglobin in Buffer Solutions", J. Phys. Chem. B., vol. 111, No. 26, pp. 7656-7664 (2007).
Mandal et al. "Spectroscopic investigations to reveal the nature of interactions between the haem protein myoglobin and the dye rhodamine 6G'," Luminescence, vol. 27, No. 4, pp. 285-291 (2012).
Mukherjee et al., "Characterization of the Interactions of Fluorescent Probes with Proteins: Coumarin 153 and 1,8-ANS in Complex with Holo- and Apomyoglobin", Photochemistry and Photobiology, vol. 82, No. 6, pp. 1586-1590 (2006).
Nakazumi et al. "Near-infrared luminescent bis-squaraine dyes linked by a thiophene or pyrene spacer for noncovalent protein labeling," Synthetic Metals, vol. 153, No. 1, pp. 33-36 (2005).
Ohashi et al., "Preparation of Artificial Metalloenzymes by Insertion of Chromium(III) Schiff Base Complexes into Apomyoglobin Mutants", Angew. Chem. Int. Ed. Engl., 3; vol. 42, No. 9, pp. 1005-1008 (2003).
Patonay et al., "Noncovalent Labeling of Biomolecules with Red and Near-Infrared Dyes", Molecules, vol. 9, No. 3, pp. 40-49 (2004).
Santambrogio et al., "Monitoring the Tanford transition in β-lactoglobulin by 8-anilino-1-naphthalene sulfonate and mass spectrometry", Rapid Communications in Mass Spectrometry, vol. 22, pp. 4049-4054 (2008).
Stryer et al., "The Interaction of a Naphthalene Dye with Apomyoglobin and Apohemoglobin. A Fluorescent Probe of Nonpolar Binding Sites", J. Mol. Biol., vol. 13, No. 2, pp. 482-495 (1965).

* cited by examiner

*Primary Examiner* — Karen Cochrane Carlson
(74) *Attorney, Agent, or Firm* — Bozicevic, Field & Francis LLP; Bret E. Field

(57) ABSTRACT

Chromophore compositions and methods of making and using the same are provided. Aspects of the chromophore compositions include a chromophore component having a chromophore, such as a fluorescent dye moiety, stably associated with a prosthetic group binding cavity of a metalloprotein. Also provided are methods of making, methods of use, systems and kits related to the subject fluorescent compositions.

15 Claims, 9 Drawing Sheets

```
         10         20         30         40         50         60
MGHHHHHHHH HHHHGGDDDD KGSTSFDGLS DGEWQLVLNV WGKVEADIPG HGQEVLIRLF
         70         80         90        100        110        120
KGHPETLEKF DKFKHLKSED EMKASEDLKK ASACVLTALG GILKKKGHHE AEIKPLAQCF
        130        140        150        160        170        180
ATKHKIPVKY LEFISECIIQ VLQSKHPGDF GADAQGAMNK ALELFRKDMA SNYKELGFQG
```

SEQ ID NO:01

FIG. 8

CHROMOPHORE COMPOSITIONS AND METHODS OF MAKING AND USING THE SAME

CROSS-REFERENCE TO RELATED APPLICATIONS

Pursuant to 35 U.S.C. §119(e), this application claims priority to the filing date of U.S. Provisional Patent Application Ser. No. 61/763,097 filed Feb. 11, 2013, the disclosure of which application is herein incorporated by reference.

INTRODUCTION

Fluorescent labeling reagents have become increasingly useful investigative tools. The wider use of fluorescently labeled probes has resulted partly from advances in instrumentation and partly from the availability of new and improved fluorescent dyes. The squaraine dyes have received particular interest since they are a class of environmentally sensitive organic dyes showing intense fluorescence, typically in the red and near infrared region (absorption maxima are found between 630 and 670 nm and their emission maxima are between 650-700 nm). They are characterized by their unique aromatic four membered ring system, and are derived from squaric acid.

SUMMARY

Chromophore compositions and methods of making and using the same are provided. Aspects of the compositions include a chromophore component having a chromophore, such as a fluorescent dye moiety, stably associated with a prosthetic group binding cavity of a metalloprotein. Also provided are methods of making, methods of use, systems and kits related to the subject fluorescent compositions.

In certain aspects, a method for encapsulating a dye in the apo form of a heme-protein comprises providing an apo form a heme-protein comprising a heme binding site, contacting a fluorescent dye to the protein wherein the dye has an affinity for the heme binding site, and then reacting the dye-protein complex with a crosslinking reagent to encapsulate or lock the dye in the protein. In some embodiments, the protein may be genetically modified to increase the affinity of the dye for the heme binding site relative to an affinity of a heme moiety for the same heme binding site and/or to facilitate the formation of internal crosslinks. In some embodiments the modification comprises replacing at least a histidine amino acid with an amino acid selected from the group comprising alanine, leucine, phenylalanine and tryptophan. In some embodiments the method may further comprise reacting the protein with a crosslinking reagent to generate an internal crosslink in the heme-protein after the dye is bound at the heme binding site. The crosslinking reagent may be bis(sulfosuccinimidyl) BSOCOES (Bis[2-(succinimidooxycarbonyloxy)ethyl]sulfone), DMA (Dimethyl adipimidate.2 HCl, DMP (Dimethyl pimelimidate.2 HCl), DMS (Dimethyl Suberimidate.2 HCl), DSG (Disuccinimidyl glutarate), DSP (Dithiobis[succinimidyl propionate]), DSS (Disuccinimidyl suberate), DST (Disuccinimidyl tartarate), DTBP (Dimethyl 3,3'-dithiobispropionimidate.2 HCl), or DTSSP (3,3'-Dithiobis[sulfosuccinimidylpropionate]).

Internal crosslinks may be formed by genetically modifying the heme-protein to replace any non-cysteine amino acid in the heme-protein with a cysteine amino acid and then reacting the genetically modified heme-protein with a crosslinking reagent, such as a reagent from the bismalamide family. In some embodiments the crosslinking reagent may be bis(malemido)ethane (BMOE), 1,4-bis(maleimido)butane (BMB) or bis(maleimido)hexane (BMH). In certain aspects, the heme-protein may be myoglobin or hemoglobin. In some embodiments the fluorescent dye may has a first quantum yield in an organic solvent that is at least 50 times higher than a second quantum yield in an aqueous solvent. In some embodiments the dye may be selected from Nile Red®, 2-[6-[4-(dimethylamino)phenyl]-1,3,5-hexatrienyl]-3-ethyl-benzothiazolium perchlorate (LDS 820), (2-(6-(p-dimethylaminophenyl)-2,4-neopentylene-1,3,5-hexatrienyl)-3-ethylbenzothiazolium perchlorate) (LDS 821), coumarins, fluoranthene, mono-squaraine and bis-squaraine dye.

In certain aspects, a method of labeling an antigen in a sample such as a biological or diagnostic sample may comprise encapsulating a fluorescent dye in the apo form of a heme-protein, covalently linking the heme-protein to an antigen specific antibody, contacting the antibody to the antigen and measuring the fluorescence of the fluorescent dye bound to the antigen. The antigen may be a cell surface specific marker or any antigen. The antigen may be bound to a solid support such as micro-titer plates or bead surfaces. The biological sample may comprise peripheral blood cells, urine, or saliva. In certain aspects, the heme-protein may be an apo-myoglobin or an apo-hemoglobin.

Aspects of the invention provide a composition for a fluorescence detector (e.g., flow cytometer) measurement of an antigen in a sample comprising a heme-protein conjugated to a reagent-capture particle or molecule (also referred to herein as a specific binding domain) wherein the heme-protein comprises an encapsulated fluorescent dye. In some embodiments the reagent-capture particle is an antigen specific antibody or a solid particle having an antibody-capture reagent bound to the surface of the particle. In certain aspects the fluorescent dye comprises a squaraine. In certain aspects, the heme-protein may be an apo-myoglobin or an apo-hemoglobin.

BRIEF DESCRIPTION OF THE FIGURES

FIG. 8 provides the amino acid sequence of a modified human apo-myoglobin, where modified amino acid residues are in bold.

DEFINITIONS

Before describing exemplary embodiments in greater detail, the following definitions are set forth to illustrate and define the meaning and scope of the terms used in the description.

The term 'chromophore' as used herein refers to a compound capable of being detected colorimetrically or fluorometrically. The specific examples disclosed herein describe chromophores detected by fluorescence (e.g., fluorescent dye motifs). It should be understood, however, that the compounds and methods described herein can equally be utilized with chromophores that are detected by other means, such as, for example, absorbance or phosphorescence. Chromophores contemplated for use in the practice of certain embodiments of the present invention are environmentally sensitive fluorescent dyes wherein the quantum yield of the dye is significantly greater in an organic environment relative to the quantum yield of the dye in an aqueous environment. In certain embodiments of the invention, a chromophore may be an environmentally sensitive fluorescent dye, such as a squaraine dye.

The terms "heme prosthetic group", "heme" and "hemin" are used interchangeably herein and may refer to any metal bound compound of a porphyrin chelate.

The term 'heme-protein' refers to a metalloprotein capable of binding a hemin or heme moiety. Heme-proteins are a class of metalloproteins containing a hemin prosthetic group. Heme may bind to the heme-protein, either covalently or non-covalently. By 'apo-heme-protein' it is meant a heme-protein that does not contain a prosthetic group (e.g., hemin). By 'holo-protein' it is meant a heme-protein that does contain a prosthetic group (e.g., hemin). Heme-proteins contemplated for the use in this invention are the apo form of proteins that naturally contain non-covalently bound heme or hemin. Aspects of the invention include the use of any heme-protein capable of non-covalently binding a heme group.

Figure 1:
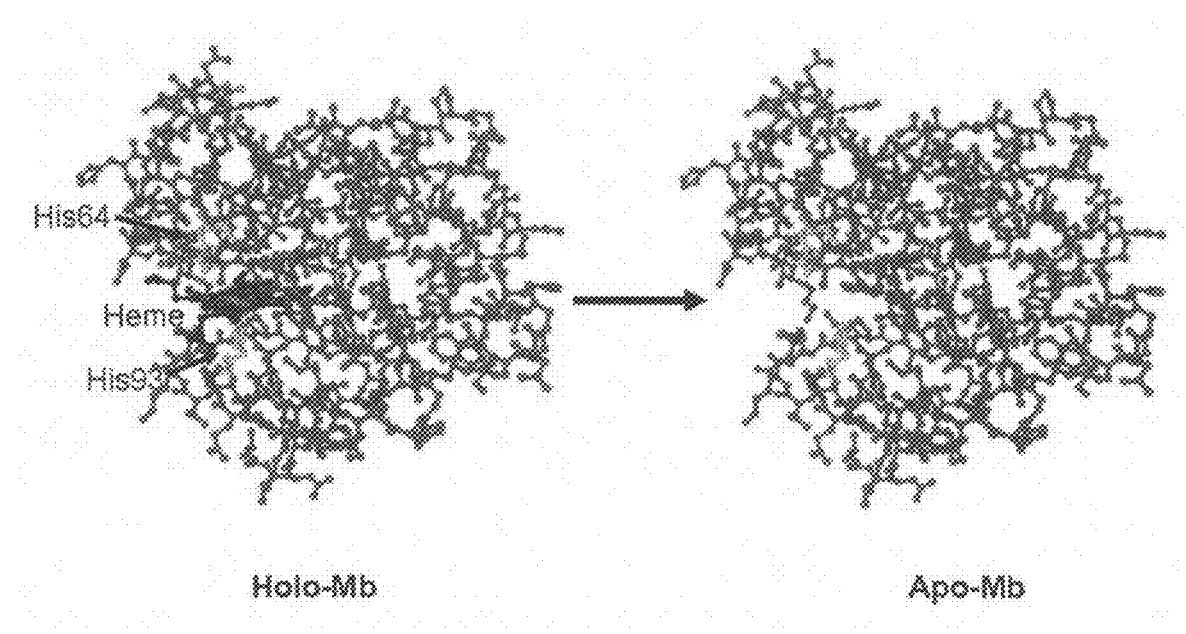
FIG. 1 shows the structures of holo-myoglobin and apo-myoglobin.

The term 'myoglobin' (abbreviated Mb) refers to an oxygen-binding protein found in the muscle tissue of vertebrates in general and in almost all mammals. It is related to hemoglobin, which is the oxygen-binding protein in blood, specifically in red blood cells. Myoglobin is a single-chain globular protein of 153 or 154 amino acid long wild-type sequence. Wild type human myoglobin has coordinating histadines (H64 and H93, as seen in FIG. 1). Myoglobin is capable of binding a heme (iron-containing porphyrin) prosthetic group in a cavity around which the remaining apoprotein folds (Holo-Mb). Apo-myoglobin is myoglobin that lacks its heme group (Apo-Mb).

The term 'squaraine' refers to a fluorescent dye characterized by an aromatic four membered ring system. Squaraine is derived from squaric acid, and may have one substitution on the four-membered aromatic ring (mono-squaraine), or two substitutions on the four-membered aromatic ring (bis-squaraine).

DETAILED DESCRIPTION

Chromophore compositions and methods of making and using the same are provided. Aspects of the chromophore compositions include a chromophore component having a chromophore, such as a fluorescent dye moiety, stably associated with a prosthetic group binding cavity of a metalloprotein. Also provided are methods of making, methods of use, systems and kits related to the subject fluorescent compositions.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The practice of the present invention may employ, unless otherwise indicated, conventional techniques from molecular biology (including recombinant techniques), cell biology, immunoassay technology, microscopy, image analysis, and analytical chemistry, which are within the skill of the art. Such conventional techniques include, but are not limited to, detection of fluorescent signals, image analysis, selection of illumination sources and optical signal detection components, labeling of biological cells, and the like. Such conventional techniques and descriptions can be found in standard laboratory manuals such as Genome Analysis: A Laboratory Manual Series (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press); Murphy, Fundamentals of Light Microscopy and Electronic Imaging (Wiley-Liss, 2001); Shapiro, Practical Flow Cytometry, Fourth Edition (Wiley-Liss, 2003); Herman et al, Fluorescence Microscopy, 2nd Edition (Springer, 1998); all of which are herein incorporated in their entirety by reference for all purposes.

In further describing embodiments of the invention, aspects of embodiments of the compositions and methods for their fabrication will be described first in greater detail. Next, embodiments of methods of using the compositions, as well as systems and kits that may be used in practicing methods of the invention, are reviewed in greater detail.

Compositions

As summarized above, compositions of the invention are chromophore compositions that include a chromophore stably associated with a prosthetic group binding cavity of a metalloprotein. Each of these components is now described in greater detail.

Metalloprotein Component

As summarized above, the compositions include a metalloprotein having a prosthetic group binding cavity. The term 'metalloprotein' refers to a protein having a metal ion in its structure, e.g., as provided by a prosthetic group. Metalloproteins of interest are proteins having a prosthetic group binding cavity. A wild-type metalloprotein is capable of binding a prosthetic group having one or more metal ions. The prosthetic group binding cavity may, in a wild type metalloprotein, be capable of associating with (e.g., binding to, encapsulating, folding around, etc.) a prosthetic group.

Depending on the nature of the metalloprotein, the prosthetic group binding cavity may vary greatly. Prosthetic groups for which the binding cavity of the matalloprotein of interest (or at least in the wild type version thereof) include, but are not limited to macrocyclic ligands, such as ligands having a ring of 8 or more, 9 or more, or 10 or more atoms. For example, the prosthetic group may be a heterocyclic organic ring, such as porphyrin. When present as part of the metalloprotein, the prosthetic group may include one or more metal ions (e.g., complexed to atoms of a heterocyclic organic ring). In certain embodiments, the prosthetic group may be a heme compound.

By prosthetic group binding cavity is meant a hollow space, e.g., pit or indentation, in the three dimensional structure of the metalloprotein that, at least in the wild type version of the metalloprotein of interest, is configured to at least partially house or encompass a prosthetic group to thereby stably associate with the prosthetic group. The volume of the prosthetic group binding cavity of the metalloprotein may vary, ranging in some instances from 50 $nm^3$ to 1,000 $nm^3$, such as 2500 $nm^3$ to 1000 $nm^3$, an including 500 $nm^3$ to 1,000 $nm^3$, wherein in some instances the volume of the binding cavity is 100 $nm^3$ or more, such as 250 $nm^3$ or more, and including 500 $nm^3$ or more, and in some instances the volume is 1,000 $nm^3$ or less, such as 1750 $nm^3$ or less. The prosthetic group may associate with the prosthetic group binding cavity of a wild type metalloprotein by any of a number of non-covalent interactions, such as non-polar, polar, and ionic interactions, which provide for association of the prosthetic group with the metalloprotein. As indicated above, the prosthetic group binding cavity may be capable of encompassing all or part of the prosthetic group.

Metalloproteins of interest include animal metalloproteins, e.g., vertebrate metalloproteins, including fish, amphibian, reptile, bird and a mammalian metalloproteins. In some instances, the metalloprotein is a mammalian metalloprotein. The terms "mammal" or "mammalian," where are used broadly to describe organisms which are within the class mammalia, including the orders carnivore (e.g., dogs and cats), rodentia (e.g., mice, guinea pigs, and rats), ungulates (e.g., horses, cows, pigs), whales, and primates (e.g., humans, chimpanzees, and monkeys).

The metalloprotein of the compositions described herein may be a wild-type protein or a homologue or mutant thereof. Homologs or proteins (or fragments thereof) that vary in sequence from wild type amino acid sequences metalloproteins as described herein are found in compositions of the invention in certain embodiments. By homolog is meant a protein having 10% or more, such as 20% or more and including 30% or more, and in some instances 35% or more, such as 40% or more and including 60% or more amino acid sequence identity to a wild type metalloprotein of interest (such as a wild type heme-protein, e.g., a wild type apomyoglobin, such as a wild type mammalian apomyoglobin, e.g., human apomyoglobin), e.g., as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151-153. (Parameters used are ktuple 1, gap penalty 3, window, 5 and diagonals saved 5). In some embodiments, homologues of interest have much higher sequence identify to a corresponding wild type protein, e.g., 65%, 70%, 75%, 80%, 85%, 90% or higher. Also provided are proteins that are substantially identical to the wild type protein, where by substantially identical is meant that the protein has an amino acid sequence identity to the sequence of wild type protein of 60% or more, such as 65% or more and including 70% or more, where in some instances the identity may be much higher, e.g., 75%, 80%, 85%, 90%, 95% or higher.

Proteins which are mutants of the naturally occurring proteins are also present in compositions of invention according to certain embodiments. Mutants include single amino acid changes, deletions of one or more amino acids, insertions of one or more amino acids, N-terminal truncations, C-terminal truncations, etc. Mutants can be generated using standard techniques of molecular biology, e.g., random mutagenesis, and targeted mutagenesis.

In certain aspects, the metalloprotein of the subject compositions is a heme-binding protein (or "heme-protein") that binds to a heme prosthetic group, or mutant of a such a heme-binding protein. An 'apo' heme-protein is a heme-protein that does not contain a prosthetic group (e.g., hemin). A 'holo' heme-protein is a heme-protein that does contain a prosthetic group (e.g., hemin). Heme-proteins provided in the embodiments herein may be the apo form of proteins that would naturally contain non-covalently bound heme or hemin, or mutants of such proteins, as reviewed in greater detail below. In some embodiments, the heme-binding protein may be a hemoglobin or a myoglobin. In some embodiments the heme-protein may be apomyoglobin (Apo-Mb) or apohemoglobin (Apo-Hb). The heme-protein may have a naturally occurring (wild type) amino acid sequence. For example, the heme-protein may have the sequence of a naturally occurring mammalian apomyoglobin, such as human, mouse, horse, whale, or pig apomyoglobin. The genbank accession numbers of apomyoglobin protein sequences of interest include, but are not limited to: NP_976312.1, NP_976311.1, NP_005359.1, CAA25109.1, AAH14547.1, NP_005359.1, NP_067599.1, NP_001157520.1, NP_038621.2, NP_001157488.1, NP_999401.1, AAA31073.1, NP_776306.1, NP_001161224.1, NP_001072126.1, ABN71515.1, NP_001274714.1, NP_001273527.1, ADQ74520.1, ADQ74518.1, ADQ74517.1, ADQ74514.1, ADQ74513.1, ADQ74511.1, ADQ74510.1, ADQ74507.1, CAA27994.1, NP_956880.1, AAH56727.1, AAR00323.1, 101M_A, NP_001125556.1, NP_001165333.1, NP_001187526.1, NP_001266612.1, NP_001273527.1, NP_001274714.1, AGM75765.1, AGM75763.1, AGM75762.1, AGM75761.1, AGM75760.1, AGM75759.1, AGM75770.1, XP_001081975.2, XP_001156646.1, BAF03579.1, and the like.

As reviewed above, in some instances the metalloprotein component of the compositions may be a mutant metalloprotein. As such, also of interest are mutants of wild type heme-proteins, e.g., as described above. Metalloproteins found in some instances of the compositions are mutants of mammalian apomyoglobins, i.e., apomyoglobin proteins that include one or more mutations, such as described above, as compared to a wild-type protein. The mutations may vary, where mutations of interest include substitution, deletion, insertion, and point mutations which result in a modified amino acid sequence, as compared to a reference wild type sequence.

In certain aspects, a mutation may be a point mutation. In some embodiments, the point mutation may include (result in) a substitution of a cysteine residue for a naturally occurring amino acid residue. The substituted cysteine residue may be proximal to or within the prosthetic group binding cavity of the metalloprotein. In some embodiments, a point mutation may include a substitution of a non-histidine residue for a naturally occurring histidine residue. For example, the non-histidine residues may be selected from the group including alanine, leucine, phenlalanine, tryptophan. In some embodiments, the mutation may include a substitution of a non-histidine residue for a heme coordinating histidine residue, such as H64 and H93 of human myoglobin, e.g., as seen in FIG. 1. In this example, the mutation may improve an association of the fluorescent dye moiety with the prosthetic binding group cavity (heme binding site). The mutation may, alternatively or in addition, decrease an affinity of the heme binding site for heme.

In certain aspects, the metalloprotein may be an apomyoglobin having a mutation altering the protein structure, cavity size, affinity of the heme-binding site (i.e. cavity) to heme, affinity of the heme-binding site to a fluorescent dye moiety, having a mutation that enhance an internal crosslinking upon exposure of the myoglobin to a crosslinking reagent, or any combination thereof. For example, the apomyoglobin may be a human myoglobin or a myoglobin of another animal, wherein one or more amino acid residues are replaced at any of the following positions (starting after the initiator methionine): Trp 14, Lys 16, His 24, Gln 26, Val 28 (or Ile 28 in certain non-human species), Leu 29, Ile 30, Phe 33, Lys 34, His 36, Phe 43, Asp 44, Lys 45 (or Arg 45 in certain non-human species), Phe 46, Lys 56, Asp 60, Leu 61, His 64, Thr 67, Val 68, Leu 69, Ala 71, Leu 89, Gln 91, Ile 99, Leu 104, Ile 107 (or Leu 107 in certain non-human species), Ser 108, His 119, Leu 137, and Phe 138. In certain aspects, a non-histidine amino acid, such as alanine, leucine, phenylalanine or tryptophan, may replace a histidine, such as His 24, His 36, His 64, and His 119 of the above example. In certain aspects, one or more of the amino acid residues Val 28 (or Ile 28 in certain non-human species), Val 68, Ile 107, Leu 89, Leu 104, and Phe 138 may be replaced with another amino acid, such as tryptophan. In certain aspects, a substitution of an amino acid of the apomyoglobin, such as any listed in the above, may enhance an internal crosslinking upon exposure of the apomyoglobin to a crosslinking reagent. For example, a cysteine residue may be substituted for any of the previously listed amino acids. Alternatively or in addition, a lysine residue may be substituted for any of the above-listed amino acids. Discussion of mutations of myoglobin that may be suitable to embodiments described herein may be found in, among other locations, "Discovery of new ligand binding pathways in myoglobin by random mutagenesis" (Huang et al. *Nature* Structural Biology 1994; 1, 226-229.

In certain aspects, the metalloprotein (e.g., the heme-binding protein) may have a tag, such as a His tag, CBP, MBP, GST, or other tag for affinity purification.

An example of a mutant human apomyoglobin of interest in certain embodiments is a protein having the sequence shown in FIG. 8 (i.e., SEQ ID NO:01). As illustrated in FIG. 8, amino acids 3 to 14 are of a histidine tag enabling purification by Ni-NTA affinity. M27 of the illustrated sequence corresponds to the initiator methionine of the wild-type human myoglobin sequence. Amino acids 28 to 180 correspond to a human myoglobin sequence of 153 amino acids with the following mutations: H64 of the wild-type sequence has been replaced with alanine (A91 of SEQ ID NO:01); H93 of the wild-type sequence has been replaced with phenylalanine (F120 of SEQ ID NO:01); and amino acid residues above and below the edge of the heme-binding site were replaced with cysteines (C94 and C119 of SEQ ID NO:01). In certain aspects, the metalloprotein may include the amino acid sequence starting with M27 or G28 of SEQ ID NO:01.

Chromophore Component

As summarized above, compositions as described herein further include a chromophore. As reviewed above, the chromophore may be any compound capable of being detected colorimetrically or fluorometrically. The specific examples disclosed herein describe chromophores detected by fluorescence. It should be understood, however, that the compounds and methods described can equally be utilized with chromophores that are detected by other means readily available to those skilled in the art, such as, for example, absorbance or phosphorescence.

Chromophores of interest include fluorescent dye moieties. The fluorescent dye moiety may be any suitable molecule that fluoresces when associated with the metalloprotein. In certain aspects, the fluorescent dye moiety is a non-protein organic fluorophore. The molecular weight of the non-protein organic fluorophore may vary, ranging in some instances from 50 Da to 5 kDa, such as 100 Da to 1 kDa, including 200 Da to 500 Da.

In certain embodiments, a non-protein organic fluorophore may include a molecule belonging to any of the following chemical families: xanthene derivatives (such as fluorescein, rhodamine, Oregon green, eosin, Texas red, etc.); fluorescein derivatives (such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC)); acridine derivatives (such as acridine orange, acridine yellow, acridine red, acridine isothiocyanate, proflavin, etc.); quinone-imine derivatives (such as azines, oxazines, and thiazines); cyanine derivatives (such as cyanine, indocarbocyanine, oxacarbocyanine, thiacarbocyanine, merocyanine, etc.); naphthalene derivatives (such as dansyl and prodan derivatives); coumarin and derivatives thereof (e.g., 7-amino-4-methylcoumarin (i.e., AMC, Coumarin 120), 7-amino-4-trifluoromethylcouluarin (i.e., coumaran 151)); azo derivatives; oxadiazole derivatives (such as pyridyloxazole, nitrobenzoxadiazole benzoxadiazole, etc.); anthracene derivatives; anthraquinones (such as DRAQ5, DRAQ7 CyTRAK Orange, etc.); pyrene derivatives (such as pyrene butyrate, succinimidyl 1-pyrene butyrate, cascade blue, etc.); oxazine derivatives (such as Nile red, Nile blue, cresyl violet, oxazine 170, etc.); arylmethane derivatives (such as auramine, crystal violet, malachite green, etc.); tetrapyrrole derivatives (such as porphin, phthalocyanine, bilirubin, etc.); squaraines (e.g., bis-squaring, mono-squaraine), squarylium, 2-[6-[4-(dimethylamino)phenyl]-1,3,5-hexatrienyl]-3-ethyl-benzothiazolium perchlorate (LDS 820), (2-(6-(p-dimethylaminophenyl)-2,4-neopentylene-1,3, 5-hexatrienyl)-3-ethylbenzothiazolium perchlorate) (LDS 821), fluoranthene, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS; anthranilamide, 5',5"-dibromopyrogallol-sulfonephthalein (Bromopyrogallol Red); diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL); 4-dimethylaminophenylazophenyl-4'-isothiocyanate (DABITC), erythrosin and derivatives thereof (such as erythrosin B and erythrosin isothiocyanate), fluorescamine and derivatives thereof, Malachite Green isothiocyanate, 4-methylumbelliferone, ortho cresolphthalein, nitrotyrosine, pararosaniline, Phenol Red, B-phycoerythrin, o-phthaldialdehyde, Reactive Red 4 (Cibacron™ Brilliant Red 3B-A), rosolic acid and terbium chelate derivatives, and so forth. A number of dyes are described in "Fluorescent Dyes and Their Supramolecular Host/Guest Complexes with Macrocycles in Aqueous Solution" (Dsouza et al. *Chem. Rev.* 2011, 111, 7941-7980), where such dyes may be present in compositions described herein. In addition, the non-protein organic fluorophore may include one or more macrocyclic ligands.

Figure 4A:
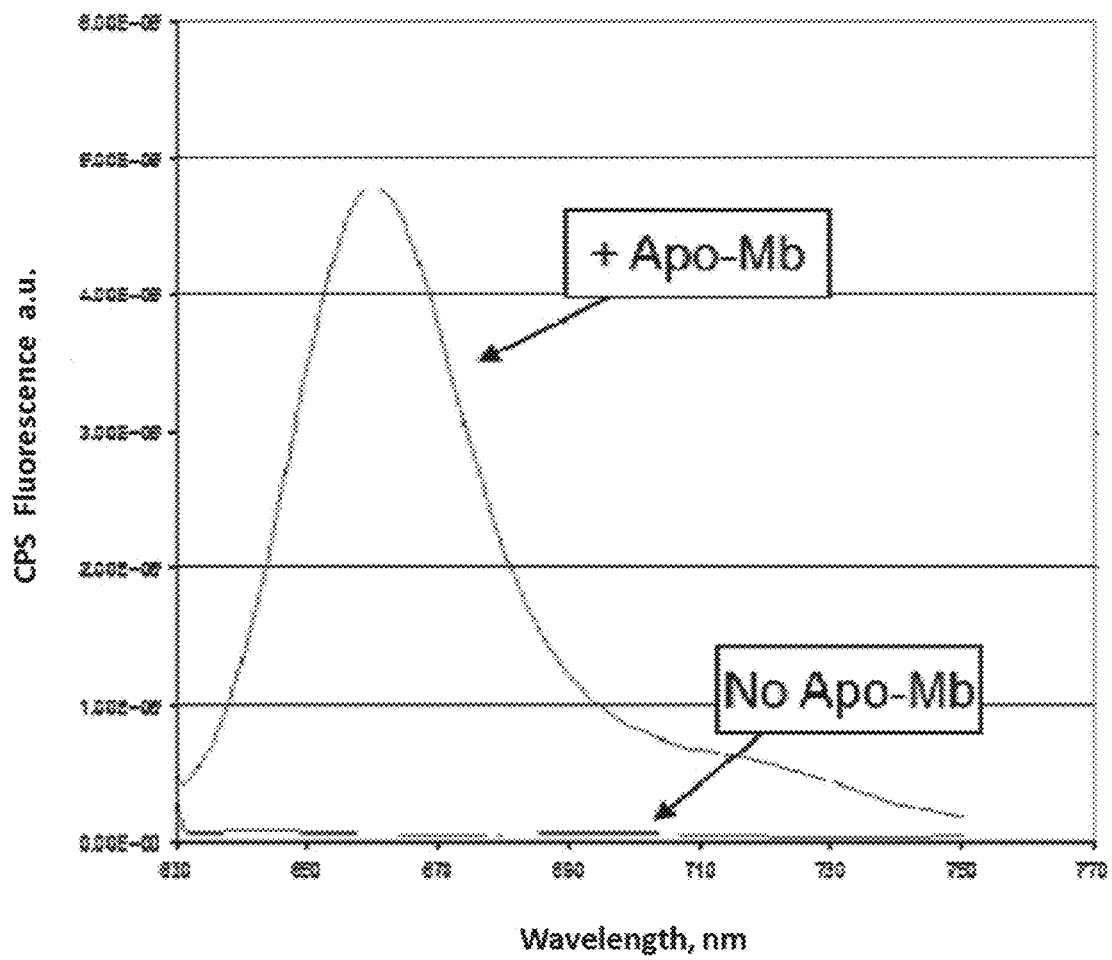
FIG. 4A provides a graph demonstrating the fluorescence of bis-squaraine in the presence and absence of apo-myoglobin.
Figure 4B:
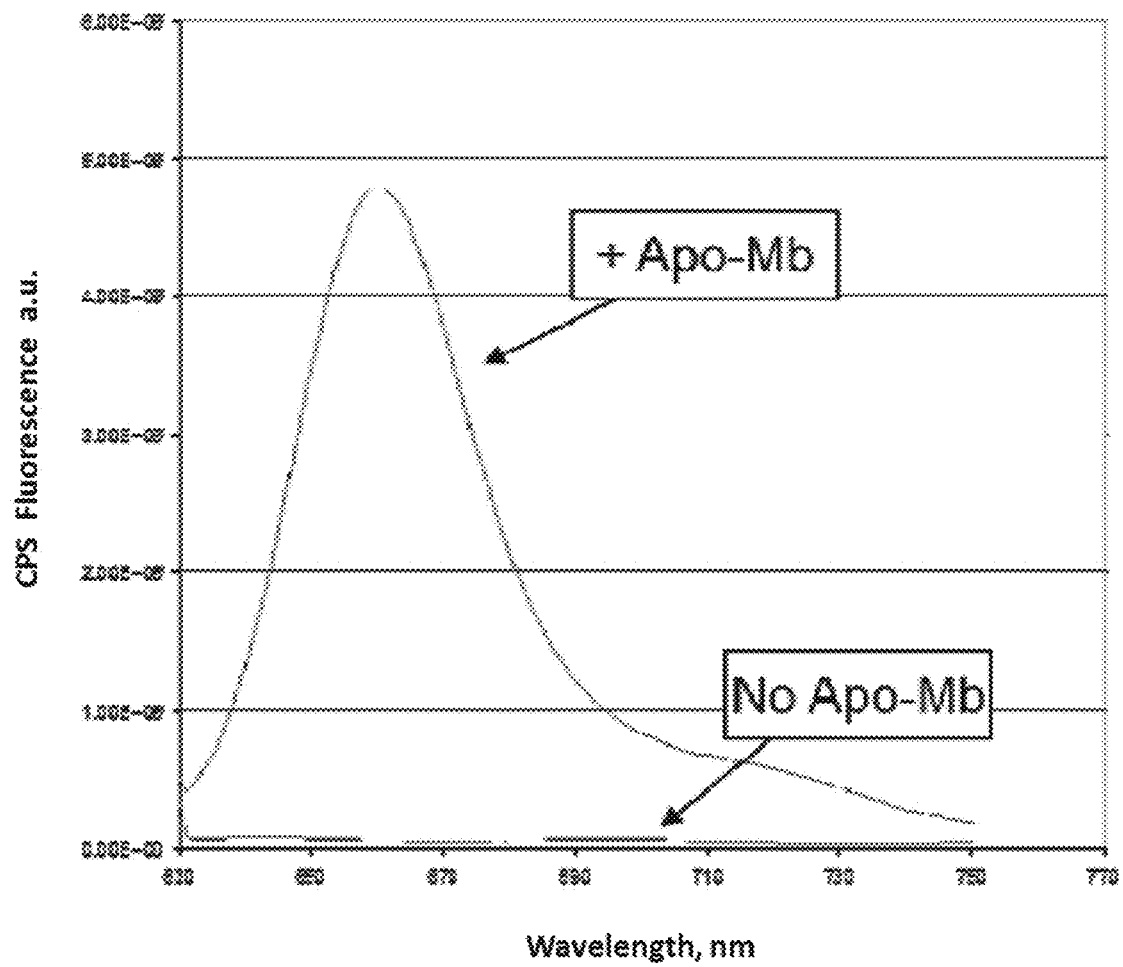
FIG. 4B provides a graph demonstrating the fluorescence of mono-squaraine in the presence and absence of apo-myoglobin.

In certain aspects, the fluorescent dye moiety (e.g., non-protein organic fluorophore) may be an environmentally sensitive fluorophore. For example, the fluorescent dye moiety may be insoluble in an aqueous environment or may demonstrate low solubility in an aqueous environment. The environmentally sensitive fluorophore may exhibit at least one of a fluorescence excitation spectrum, a fluorescence emission spectrum, a fluorescence intensity (e.g., quantum yield), and a fluorescence lifetime that differs depending on the environment (e.g., an aqueous vs. an organic environment, the pH of the environment, etc.) in which it is present. For example, an environmentally sensitive fluorophore may have a fluorescence intensity (e.g., a quantum yield for a given excitation wavelength, intensity of a fluorescence emission maxima, etc.) that is higher when the fluorophore is in an organic as compared to an aqueous environment. In certain embodiments, an environmentally sensitive fluorophore stably associated with the prosthetic group binding cavity of the metalloprotein as found in compositions of the invention may have a first fluorescence intensity that is higher (e.g., 50 times higher or more) than a second fluorescence intensity of the environmentally sensitive fluorophore free in aqueous solution. For example, the first fluorescence intensity may be at least 5 times higher, at least 10 times higher, at least 20 times higher, at least 50 times higher, at least 100 times higher, or at least 200 times higher than the second fluorescence intensity. An example of such a fluorophore (i.e., fluorescent dye moiety) is illustrated in FIG. 4, where FIG. 4A and FIG. 4B show the fluorescence of bis-squaraine (A) and mono-squaraine (B) in an aqueous solution in the presence and absence of apomyoglobin. It can be seen that upon binding to apomyoglobin, the squaraine dyes show a greater than 50 fold increase in fluorescence in the 630 to 700 nm range.

In certain aspects, a chromophore that binds to a heme-protein may be utilized in the subject compositions. The chromophore may be an environmentally sensitive fluorescent molecule wherein the quantum yield of the molecule is greater (e.g., greater than 5, 10, 50, or 1000 times) in an organic environment relative to the quantum yield of the molecule in an aqueous environment.

In certain embodiments, an environmentally sensitive fluorophore may be a derivative of squaraine, dapoxyl, coumarin, cucurmin, badan, DMABN, HMPO, ThT (thioflavin T), bisimides (e.g., DBN), styrlpyridinium (e.g., 2-ASP, 4-ASP), benzimidazole (e.g., BEA, MBC, bis-benzimidazole), 2-styrylindolium dye (e.g., STIND1, STIND2), ADMP, DAPS, cucurbiturils, adamantlyl, naphthalimides, 1,8-1-anilinonaphthalene-8-sulfonic acid (1,8-ANS), 2-anilinonaphthalene-6-sulfonic acid (2,6-ANS), 2-(p-toluidinyl), naphthalene-6-sulfonic acid (2,6-TNS), 6-propionyl-2-dimethylaminonaphthalene (PRODAN), or any other suitable environmentally sensitive fluorophore, such as those described by Dsouza et al. (*Chem. Rev.* 2011, 111, 7941-7980).

Figure 3A:
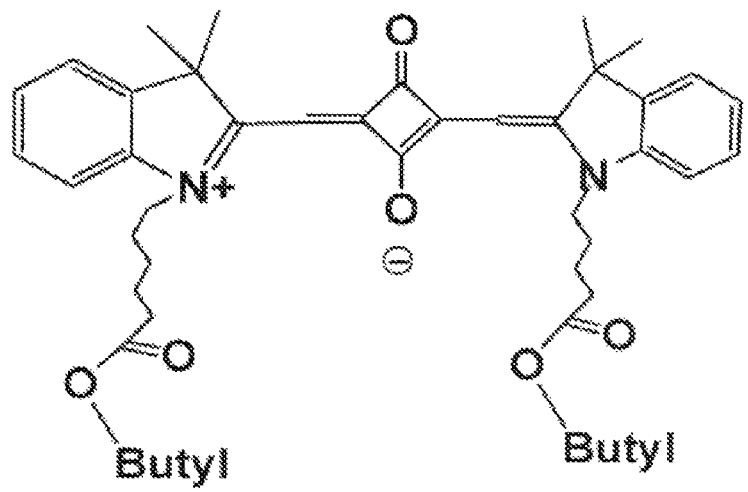
FIG. 3A provides an exemplary chemical structure of a bis-squaraine.
Figure 3B:
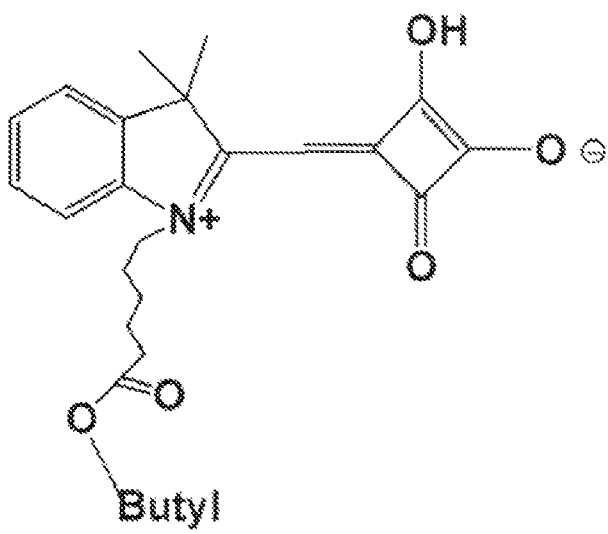
FIG. 3B provides an exemplary chemical structure of a mono-squaraine.

In certain aspects, the environmentally sensitive fluorophore may be a squaraine, characterized by a four-membered aromatic ring. Squaraine may be derived from squaric acid, and may have one substitution (mono-squaraine) or two substitutions (bis-squaraine). A Bis-squaraine may be either symmetric or asymmetric. Examples of chemical structures of a bis-squaraine and a mono-squaraine are presented in FIGS. 3A and 3B respectively. Any suitable squaraine may be used in the subject embodiments, including those described by "13-Cyclodextrin as a photosensitizer carrier: Effect on photophysical properties and chemical reactivity of squaraine dyes" (K. T. Arun et al. *J. Phys. Chem. B.* 2011, 115, 7122-7128), described by Dsouza et al. (*Chem. Rev.* 2011, 111, 7941-7980), and provided by suppliers such as Sigma-Aldrich and other chemical suppliers.

Metalloprotein-Chromophore Component

As summarized above, compositions of the invention include a chromophore, such as a fluorescent dye moiety, stably associated with a prosthetic binding cavity of a metalloprotein or mutant thereof. By stably associated is meant that the chromophore component is not displaced from the metalloprotein, at least under conditions of intended use, e.g., when employed in methods as described in greater detail below.

Figure 5A:
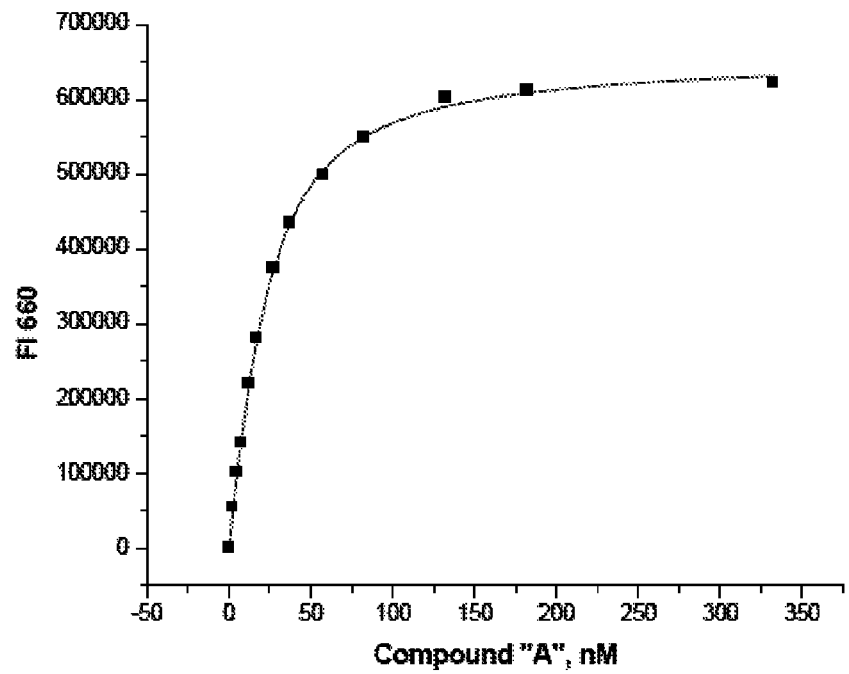
FIG. 5A and FIG. 5B show graphs demonstrating the binding curves of bis-squaraine (FIG. 5A) and mono-squaraine (FIG. 5B) to apo-myoglobin as measured by the increased fluorescence of the dyes upon binding to the protein.
Figure 5B:
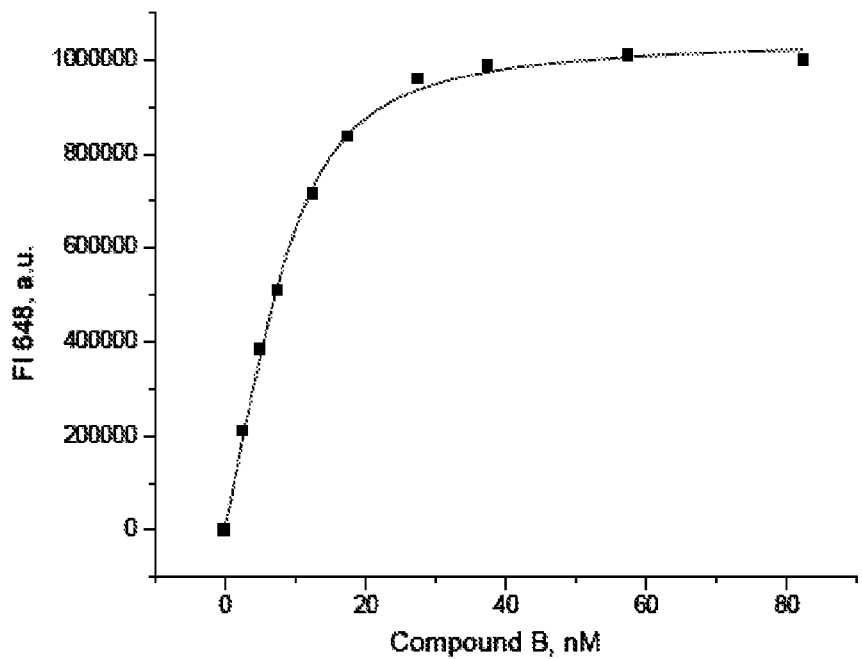

The fluorescent dye moiety may be non-covalently bound to the prosthetic group binding cavity (such as by non-polar interactions, polar interactions, ionic interactions, steric hindrance, etc.). In certain aspects, the fluorescent dye moiety may be stably associated with the prosthetic group binding cavity of the metalloprotein. A stable association between the fluorescent dye moiety and the metalloprotein may be characterized by a $K_d$ of 1 mM or less, 100 μM or less, 10

µM or less, 1 µM or less, 100 nM or less, 10 nM or less, 1 nM or less, 100 µM or less, 10 µM or less, and so forth. FIG. 5A and FIG. 5B demonstrate that the binding constants of the environmentally sensitive dyes to the heme proteins may be measured by monitoring the increased fluorescence of the dye upon binding to the apo-heme protein. Molecular modeling studies and the experimentally determined Kd for bis-squaraine, and mono-squaraine (2-20 nM) demonstrate a strong affinity of the fluorescent molecules for the heme binding site of apo-Mb.

Figure 6:
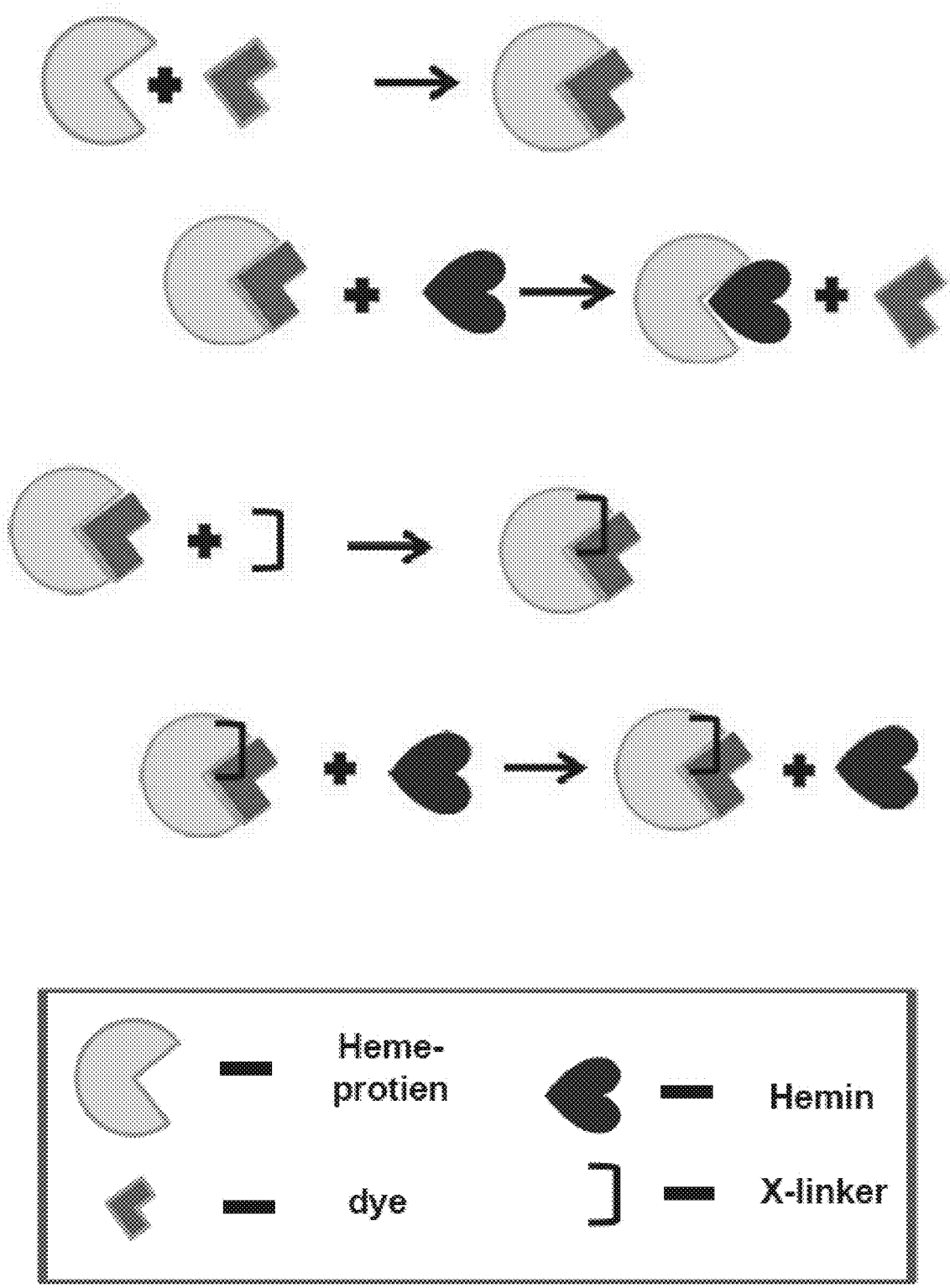
FIG. 6 shows schematic diagrams of the following: 1) binding of a dye to the heme binding site of a heme-protein; 2) displacement of the dye by a hemin molecule; 3) internal crosslinking of the dye bound protein; and 4) resistance of dye displacement by hemin when the protein encapsulate is internally cross-linked.
Figure 7:
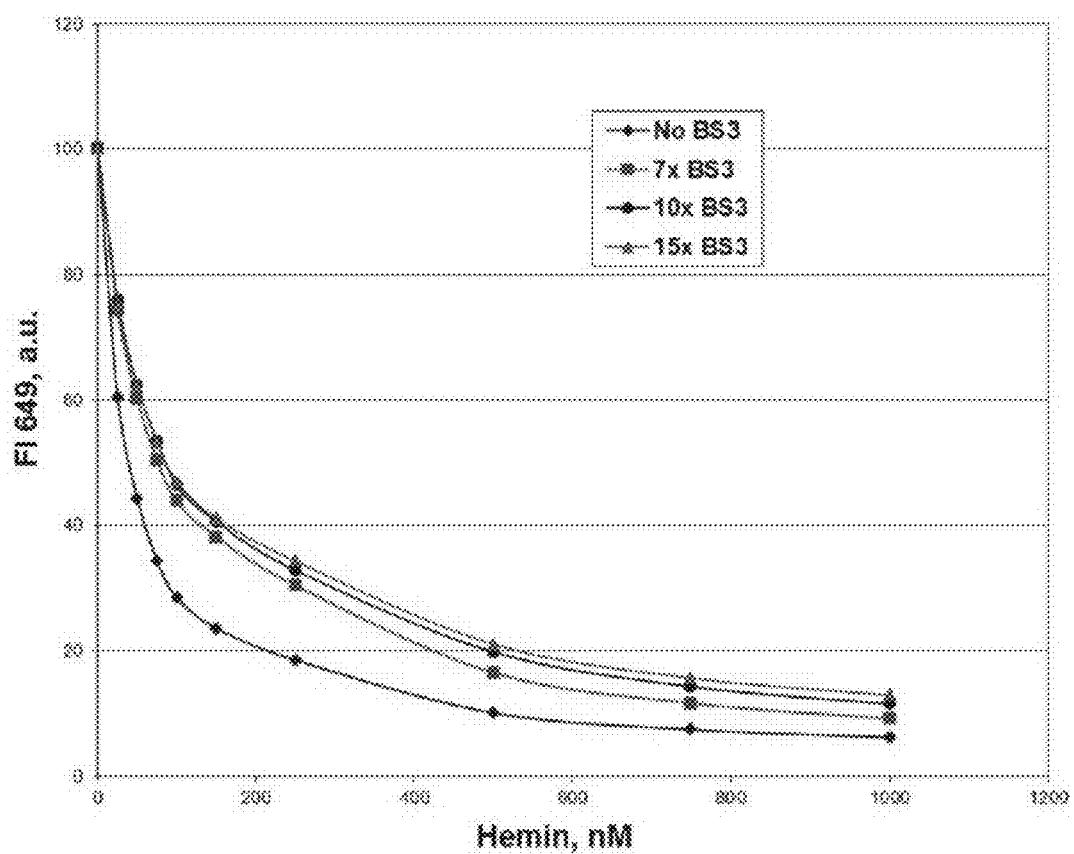
FIG. 7 shows titration plots of hemin titrating out monosquaraine encapsulated in apo-myoglobin in the absence and presence of a crosslinking reagent.

In certain aspects, the association of the fluorescent dye moiety with the cavity may be enhanced by a stabilizing modification. Stabilizing modifications are modifications of the metalloprotein that are made to enhance the association of the chromophore with the metalloprotein, and increase the stability of the association of these two components with each other relative to a control, at least to a measurable extent. The stabilizing modification may vary, and in some instances may be an internal crosslinking of amino acid residues of the metalloprotein. Internal crosslinkings of interest are those which serve to secure the association of the dye moiety in the cavity, and thereby enhance the stable associate of dye moiety with the metalloprotein. Any convenient residues may be joined to each other to provide the desired crosslinking. Residues of interest include those which are proximal to the prosthetic group binding cavity and are amenable to crosslinking. In one aspect, the internal crosslinking may include crosslinked cysteine residues. The internal crosslinking may alternatively or additionally include crosslinked lysine residues. A list of crosslinking reagents and protocols is described in, among other locations, the website made by placing "https://www." before "biochem.wisc.edu/faculty/weibel/lab/methods/Crosslinking_Reagents_Pierce.pdf". Specific crosslinking reagents of interest include, but are not limited to: bis(sulfosuccinimidyl) BSOCOES (Bis[2-(succinimidooxycarbonyloxy) ethyl]sulfone), DMA (Dimethyl adipimidate.2 HCl, DMP (Dimethyl pimelimidate.2 HCl), DMS (Dimethyl Suberimidate.2 HCl), DSG (Disuccinimidyl glutarate), DSP (Dithiobis[succinimidyl propionate]), DSS (Disuccinimidyl suberate), DST (Disuccinimidyl tartarate), DTBP (Dimethyl 3,3'-dithiobispropionimidate.2HCl), or DTSSP (3,3'-Dithiobis[sulfosuccinimidylpropionate]). The internal crosslinking may ensure that the fluorescent dye moiety remains bound to the cavity (e.g., the heme-binding site of a heme protein). Aspects of this invention include any number of crosslinked amino acids (e.g., one, two, three or more crosslinks) in the metalloprotein that act to non-covalently lock the protein to the docked fluorescent molecule, as seen in FIG. 6 and FIG. 7.

A given chromophore composition of the invention may include a single chromophore/metalloprotein component (such as described above) or two or more such components stably associated, e.g., covalently or non-covalently bound, to each other, such as two or more, three or more, five or more, ten or more, including twenty or more such components stably associated with the each other. Where a given composition includes two or more such components, the components may be the same or different from each other, e.g., differing from each other with respect to the nature of the chromophores and/or metalloproteins.

Specific Binding Domain

In certain aspects of the invention, the composition may include one or more specific binding domains. The specific binding domain may be associated with the metalloprotein in a variety of difference ways, e.g., it may be conjugated by a linker, fused, or otherwise covalently bound to the composition, e.g., to a metalloprotein of the composition. In some aspects, the specific binding domain may have an affinity for an analyte of $K_a$ of $10^4$ $M^{-1}$ or greater, $10^5$ $M^{-1}$ or greater, $10^6$ $M^{-1}$ or greater, $10^7$ $M^{-1}$ or greater, $10^8$ $M^{-1}$ or greater, $10^9$ $M^{-1}$ or greater, $10^{10}$ $M^{-1}$ or greater, $10^{11}$ $M^{-1}$ or greater, $10^{12}$ $M^{-1}$ or greater. The composition may include a peptidic or polypeptidic moiety. In some aspects, the peptidic or polypeptidic moiety may include an antibody or a binding fragment thereof (e.g., a monovalent antibody). In some aspects, the specific binding domain may be a ligand (e.g., growth factors, streptavidin, cytokines, and so forth) that specifically binds a cell surface receptor. In some aspects, the specific binding domain may be a nucleic acid moiety (such as an aptamer).

In certain aspects of the invention, the composition may include a linker conjugated to (e.g., covalently bound to) the metalloprotein. The linker may be any linker molecule known in the art such as succinimidyl 4-(N-maleimidomethyl)-cyclohexane-1-carboxylate (SMCC), N-succinimidyl-3-(2-pyridyldithio)propionate (SPDP) or others. The linker may be functionalized (e.g., to covalently attach to an antibody or other specific binding domain) and may be bi-functional. In some aspects, the linker may be selected from one of any of the crosslinker reagents discussed in embodiments of the subject compositions.

In certain aspects, the heme-protein may be covalently conjugated to an antibody or solid support. Conjugation to an antibody or solid support may occur via any means, such as via succinimidyl 4-(N-maleimidomethyl)-cyclohexane-1-carboxylate (SMCC), N-succinimidyl-3-(2-pyridyldithio) propionate (SPDP) or via another liner molecule. The complexes of this invention may be conjugated to a solid support such as beads or columns or the like. Non-antibody proteins may also be labeled with the protein-dye complexes (e.g., fluorescent components) disclosed herein. For example, antigens (e.g. ligands for a cell surface receptor or an antibody) may be coupled via any means with the protein-dye complexes.

Methods of Making

Aspects of the invention further include methods of making any of the subject compositions, e.g., as described above. A method of producing a chromophore composition may include contacting a metalloprotein having an empty prosthetic group binding cavity with a fluorescent dye moiety in a manner sufficient for the fluorescent dye moiety to stably associate with the metalloprotein, e.g., by entering the prosthetic group binding cavity. The method may further enhancing the association of the dye moiety with the metalloprotein, e.g., by producing a stabilizing modification of the protein, such as described above.

In certain aspects, stably associating the fluorescent dye moiety with the prosthetic group binding cavity may include modifying the metalloprotein. Modifying the metalloprotein may include generating an internal crosslink in the metalloprotein after the dye enters the prosthetic group binding cavity, such as through the use of any of the crosslinker reagents discussed in embodiments of the subject compositions. In certain aspects, a cysteine residue of the metalloprotein may replace a non-cysteine residue of a naturally occurring metalloprotein. Generating the internal crosslink in the metalloprotein may include crosslinking a cysteine residue that replaces a non-cysteine residue of a naturally occurring metalloprotein. Use of alternate crosslinkers to collapse the dye cavity may be employed to ensure the dye is not displaced when used in complex blood solutions. A large family of cross-linkers may successfully connect protein/dye monomers (fluorescent components) to establish signal amplification.

The use of internal crosslinking reagents may insure that the encapsulated fluorescent molecule remains bound even in the presence of molecules capable of competitively binding to the heme site (e.g., hemin). This is schematically illustrated in FIG. 6, and supported by FIG. 7. Aspects of this invention may include any number of crosslinked amino acids (e.g., one, two, three or more crosslinks) in the protein that act to non-covalently lock the protein to the docked fluorescent molecule (e.g., at the prosthetic binding group cavity). Internal crosslinking may be achieved in any number of ways in order to lock the dye into the prosthetic binding group cavity (e.g., the heme-binding site). In some embodiments crosslinking reagents such as bis(sulfosuccinimidyl) may be reacted with the native or genetically modified protein after the fluorescent molecule has been bound to the protein. For example, human recombinant apo-Mb may be incubated with an excess of mono-squaraine in a buffer such as a buffer including 50 mM sodium phosphate buffer, 150 mM sodium chloride, pH 7.2. The sample may be incubated in the presence of a crosslinking reagent. For example, samples of the apo-Mb/mono-squaraine complex may be incubated for 2 hours with an excess of BS3 reagent (such as a 2, 7, 10, 15 or more fold excess).

As the structure of the metalloprotein may be sensitive to pH, an optimal pH range for association of the prosthetic binding cavity of the metalloprotein with the fluorescent dye motif may exist. In certain aspects, the method may include modulating pH prior to generating an internal crosslink in the metalloprotein. For example, the pH of the composition may be buffered to be anywhere from 5 to 9, such as 6 to 8, 6.5 to 7.5, 5 to 5.5, 5.5 to 6, 6 to 6.5, 6.5 to 7, 7 to 7.5, 7.5 to 8, 8 to 8.5, 8.5 to 9, and so forth.

The metalloprotein (e.g., such as a modified heme-protein) may be reacted with reagents from the bismaleimide family or any other crosslinking reagent that reacts with cysteine residues in order to form internal crosslinks in the heme protein after it is complexed with a fluorescent molecule (e.g., fluorescent dye moiety). In some embodiments the crosslinking reagent may be bis(maleimido)ethane (BMOE), 1,4-bis(maleimido)butane (BMB) or bis(maleimido)hexane (BMH). In some embodiments, the crosslinking reagent may be bis(sulfosuccinimidyl) BSOCOES (Bis[2-(succinimidooxycarbonyloxy)ethyl]sulfone) DMA (Dimethyl adipimidate.2 HCl, DMP (Dimethyl pimelimidate.2 HCl), DMS (Dimethyl Suberimidate.2 HCl), DSG (Disuccinimidyl glutarate), DSP (Dithiobis[succinimidyl propionate]), DSS (Disuccinimidyl suberate), DST (Disuccinimidyl tartarate), DTBP (Dimethyl 3,3'-dithiobispropionimidate.2 HCl), or DTSSP (3,3'-Dithiobis[sulfosuccinimidylpropionate]). Other suitable crosslinking reagents include imidoesters, N-hydroxysuccinimide-esters (NHS-esters), maleimides, paraformaldehyde, glutaraldehyde, haloacetyls, pyridyl disulfides, hydrazides, carbodiimides, aryl azides, isocyanates, vinyl sulfones and any other cross-linking reagents disclosed herein. Crosslinking reagents may include, but are not limited, to those described by U.S. publication number 20110177617, which is incorporated herein by reference.

In certain aspects, the heme-protein may be covalently conjugated to an antibody or solid support before or after the binding of the fluorescent molecule for use as a biological detection agent. Conjugation to an antibody or solid support may occur via any means such as via linker molecules known in the art such as succinimidyl 4-(N-maleimidomethyl)-cyclohexane-1-carboxylate (SMCC), N-succinimidyl-3-(2-pyridyldithio)propionate (SPDP), streptavidin, avadin, or any of the crosslinking reagents described herein. The complexes of this invention may be conjugated to a solid support such as beads or columns or the like. Non-antibody proteins can also be labeled with the protein-dye complexes disclosed herein.

Aspects of the invention further include methods of producing a metalloprotein of any of the subject compositions previously described. In certain aspects, a method of producing a metalloprotein suitable for binding to a fluorescent dye moiety may include expressing a mutant metalloprotein in a host cell, wherein the mutant metalloprotein includes a mutation in a prosthetic group binding cavity. The method may further include harvesting the mutant metalloprotein from the host cell.

In certain aspects, the metalloprotein may be a heme binding protein, such as an apomyoglobin having one or more mutations as previously described. In certain aspects, the host cell may be of any suitable bacterial strain, such as *Escherichia coli, Corynebacterium, Staphylococcus, Pseudomonas fluorescens* and so forth. Alternatively, the host cell may an animal cell, such as a mammalian cell line or a yeast strain (e.g., *Saccharomyces cerevisiae, Pichia pastoris*, etc.). The step of expressing a mutant metalloprotein in the host cell may include exposing the host cell to a vector including a nucleotide sequence encoding the mutant metalloprotein. The vector may be a plasmid, virus (e.g., a bacteriophage), or any suitable vector for expressing the nucleotide sequence. The vector may include a sequence encoding an affinity tag (such as a His tag, CBP, MBP, GST, etc.). The nucleotide sequence may be under the control of a promoter, an operator (e.g., a Tet operator), an operon (such as the Lac operon), or any combination thereof. Expression of the nucleotide sequence may be inducible or constitutive. In certain aspects, the vector may include one or more antibiotic resistance genes, and the step of expressing the metalloprotein may include exposing the host cells (i.e., a bacterial strain) to an antibiotic to select for transformed bacteria. In certain aspects, the step of expressing may further include exposing the host cell to an inducing agent (such as IPTG, Tetracycline, Doxycycline, and derivatives thereof). For example, the host cell may be a bacterial strain and the step of expressing may include transforming the host cell with a plasmid including the nucleotide sequence. Recombinant techniques and protein expression systems and methods are discussed in "Recombinant protein expression and purification: A comprehensive review of affinity tags and microbial applications" (Young et al. *Biotechnol J.* 2012, 7(5): 620-34), and "Recombinant Gene Expression: Reviews and Protocols" (Palomares et al. *Methods Mol Biol.* 2004, 267:15-52). A list of vectors and protocols is also provided at the website produced by placing "http://www." before "labome.com/method/Recombinant-Protein-Expression-Vector-Host-Systems.html".

In certain aspects, the step of harvesting the metalloprotein may include growing the host cell culture (e.g., to confluency in an adherent animal cell culture, to an OD such as an OD600 of 0.6 to 0.8, 0.8 to 1, 1 to 1.2 for an yeast or bacterial cell culture, etc.). The step of harvesting may further include generating a host cell lysate by any suitable method. The step of harvesting may still further include purifying the metalloprotein by any suitable method (e.g., size-exclusion chromatography, ion-exchange chromatography, affinity beads or chromatography such as Ni-NTA beads or column, and so forth). In certain aspects, the metalloprotein may include an affinity tag (such as a His tag, CBP, MBP, GST, and so forth) that is used to purify the protein.

The protein may be naturally occurring or modified (e.g., genetically or chemically) in any way. In some embodiments genetic modification may include modification or replacement of any amino acid in order to increase the affinity of the protein for the chromophore relative to the affinity of the protein for hemin. For example, heme binding histidine residues in the heme-protein may be replaced with any other amino acid, such as alanine, leucine, phenylalanine and tryptophan. In some embodiments the genetic modification may include the replacement of one or more non-cysteine amino acid with a cysteine amino acid in order to facilitate internal crosslinking of the protein.

In certain aspects, the method may include genetically modifying a metalloprotein nucleotide sequence to provide a sequence encoding a metalloprotein suitable for binding to a fluorescent dye moiety, prior to expressing the modified sequence in the host cell. Suitable techniques for genetically modifying the metalloprotein nucleotide sequence include but are not limited to site directed mutagenesis techniques such as cassette mutagenesis, PCR site-directed mutagenesis, whole plasmid mutagenesis. Any suitable recombinant techniques (e.g., PCR, restriction digestion and ligation, etc.) may be used to provide a vector (e.g., virus, plasmid) having the modified nucleotide sequence. The modified nucleotide sequence may include one or more mutations that result in any of the metalloproteins of the subject composition previously described.

In some embodiments non-histidine amino acids may be substituted for histidine amino acids via recombinant genetic techniques. In other embodiments cysteine amino acids may be substituted for non-cysteine amino acids via recombinant genetic techniques. Substitution of a cysteine amino acid for a non-cysteine amino acid may enhance an internal crosslinking upon exposure of the metalloprotein to a reagent from the bismaleimide family or any other crosslinking reagent that reacts with cysteine residues.

Aspects of the invention may include vectors for use in practicing the above methods.

Methods of Use

Aspects of the invention further include methods of using the subject compositions. A method of assaying a sample may include contacting the sample with a fluorescent composition including; a metalloprotein including a prosthetic group binding cavity, and a fluorescent dye moiety stably associated with the prosthetic group binding cavity. In certain aspects, the metalloprotein may include a stabilizing modification that enhances association of the dye moiety with the cavity. The fluorescent composition may be any of the subject compositions described above.

In certain aspects, the fluorescent composition may include a specific binding domain, according to any of the embodiments of the subject compositions described above. The method may further include obtaining a fluorescence signal from the sample. The fluorescence signal may be provided by the fluorescence composition (e.g., by a fluorescent dye moiety of the composition). In certain aspects, the fluorescence signal may be obtained by exposing the sample to monochromatic light or a wide range of light in the UV, visible, or infrared range of the electromagnetic spectrum. The fluorescence signal may be a fluorescence emission maxima (e.g., in the UV, visible, or infrared range). The method may further include evaluating an analyte bound by the specific binding domain, based on the fluorescence signal. In certain aspects, evaluating may include assessing the amount of the analyte in the sample. The amount of the analyte may be assessed as positively relating to the intensity of the fluorescence signal. In certain aspects, the method may include assessing the amount of a ligand as an inverse function of the intensity of the fluorescence signal, wherein the ligand competes for the analyte bound by the specific binding domain (e.g., as in the case of a competitive immunoassay).

The sample may be a biological sample, such as a cell sample. In certain aspects, the sample may include a biological fluid, such as blood (e.g., whole blood, serum, plasma), urine, saliva, and so forth. In certain aspects, the sample may be a cell sample such as a peripheral blood mononuclear cell sample, a tissue sample (e.g., a cross section of a solid tissue), a cell culture, and so forth. In some aspects, the sample may include free heme such as may be present in a blood sample.

In certain aspects, the method may involve assaying the sample by flow cytometry, microscopy (e.g., of a tissue or cell culture sample stained with the fluorescent composition), immunoassays, immunostaining, or a combination thereof. The complexes (fluorescent compositions) of the embodiments described herein can be used to label a variety of non-protein molecules. Chen and Evangelista, for example, describe a multianalyte drug assay wherein labeled morphine and phencyclidine (PCP) are used in a competitive immunoassay to detect drug levels in urine (Chen and Evangelista, Clin. Chem. 40(9):1819-1822, 1994). Antibody conjugates (e.g., fluorescent compositions including an antibody specific binding domain) can also be used for diagnostic purposes, both in vitro and in vivo. Ballou et al., for example, described a method of using antibody conjugates for the detection of tumors in vivo. (Ballou et al., Cancer Immunol. Immunother. 41(4):257-263, 1995.) Lanza et al. describe an in vitro method of diagnosing leukemia using antibody conjugates. (Lanza et al., Leuk. Lymphoma 18(Suppl. 1):25-30, 1995). In certain aspects, the specific binding domain may be a ligand (e.g., growth factors, streptavidin, cytokines, and so forth) specific for a cell surface receptor, and may be used to study ligand:receptor interactions for either research or clinical purposes.

Systems

Aspects of the invention further include systems for use in practicing the subject methods. A sample analysis system may include a flow channel loaded with a sample having a fluorescent composition. The fluorescent composition may include a metalloprotein having a prosthetic group binding cavity and a fluorescent dye moiety stably associated with the prosthetic group binding cavity. In certain aspects, the system may also include a light source configured to direct light to an assay region of the flow channel. The system may include a detector configured to receive a signal from an assay region of the flow channel, wherein the signal is provided by the fluorescent composition. Optionally further, the sample analysis system may include one or more additional detectors and/or light sources for the detection of one or more additional signals.

In certain aspects, the system may further include computer-based systems configured to detect the presence of the fluorescent signal. A "computer-based system" refers to the hardware means, software means, and data storage means used to analyze the information of the present invention. The minimum hardware of the computer-based systems of the present invention includes a central processing unit (CPU), input means, output means, and data storage means. A skilled artisan can readily appreciate that any one of the currently available computer-based system are suitable for use in the present invention. The data storage means may include any manufacture including a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In certain aspects, the system includes a flow cytometer. Flow cytometers of interest include, but are not limited to, those devices described in U.S. Pat. Nos. 4,704,891; 4,727,029; 4,745,285; 4,867,908; 5,342,790; 5,620,842; 5,627,037; 5,701,012; 5,895,922; and 6,287,791; the disclosures of which are herein incorporated by reference.

Other systems may find use in practicing the subject methods. In certain aspects, the system may be a fluorimeter or microscope loaded with a sample having a fluorescent composition of any of the embodiments discussed herein. The fluorimeter or microscope may include a light source configured to direct light to the assay region of the flow channel. The fluorimeter or microscope may also include a detector configured to receive a signal from an assay region of the flow channel, wherein the signal is provided by the fluorescent composition.

Utility

The chromophore compositions as described herein may find use in a variety of methodologies in which labeling of a sample is desirable. Such methodologies include but are not limited to cytometry, microscopy, immunoassays (e.g. competitive or non-competitive), assessment of a free analyte, assessment of receptor bound ligand, and so forth. The compositions described herein may be useful in analysis of any of a number of samples, including but not limited to biological fluids, cell culture samples, and tissue samples. In certain aspects, the chromophore compositions described herein may find use in methods where analytes are detected in a sample using fluorescent labels, such as in fluorescent activated cell sorting or analysis, immunoassays, immunostaining, and the like. FIG. 7 demonstrates that fluorescent compositions of certain embodiments disclosed herein are stable and may be used in peripheral blood samples including free hemin (e.g., the fluorescent dye motif may not be outcompeted by free hemin for the prosthetic group binding cavity of the metalloprotein).

The subject chromophore compositions may find use in enhancing the properties of certain environmentally sensitive dyes. Such dyes may exhibit undesirable fluorescence properties (e.g., excitation or emission spectrum, fluorescence lifetime, quantum yield, etc.), low solubility, or other characteristics in specific environments, such as aqueous environments, organic environments, certain pH, and certain temperatures. In some aspects, environmentally sensitive fluorescent dyes used to label antibodies used in analysis and sorting of blood cells may exhibit poor fluorescence of these molecules in an aqueous environment. Some environmentally sensitive dyes fluoresce only in a narrow range of environmental conditions. The methods and compositions discussed herein provide, among other benefits, labeling reagents that are sensitive, and easily detected, in a wider range of environmental conditions.

In addition, protein dye encapsulation systems of fluorescent molecules such as GFP, PE, APC or PerCP, may require the fluorophore be covalently linked to the protein moiety. The fluorescent composition and methods of the subject invention provide fluorescent proteins without covalent attachment of the fluorescent dye moiety. This beneficially provides for an environmentally sensitive fluorescent molecule bound in an organic environment that is soluble in an aqueous environment. The bound fluorescent molecule may not be covalently attached to the heme protein, insuring that the fluorescence properties of the molecule are not negatively impacted.

In certain embodiments of the invention, apo-Mb is a generic dye encapsulation system that allows one to define and amplify dyes by design. The light amplification system is achieved using standard cross-linking reagents. As compared to PE fluorophores, a six to ten fold increase in signal relative to size and weight may be achieved.

Embodiments wherein an environmentally sensitive dye is complexed with a heme-protein may be used in combination with an antigen-specific reagent (also referred to as a specific binding domain), and provides for the use of such dyes in a number of biological detection assays.

Kits

Aspects of the invention further include kits for use in practicing the subject methods and compositions. The compositions of the invention can be included as reagents in kits either as starting materials (e.g., such as chromophore-bound heme-protein including a bi-functional linker molecule) or pre-formed complexes (e.g., such as a chromophore-bound heme-protein conjugated to antigen specific antibody) provided for use in, for example, the methodologies described above.

A kit may include the fluorescent composition of any of the embodiments of the subject compositions. The kit may further include a container (e.g., tube, bottle, packet, etc.) for providing the fluorescent composition. In certain aspects, the fluorescent composition provided by the kit may include a linker conjugated to a metalloprotein of the fluorescent composition. The linker may be functionalized (e.g., to covalently attach to an antibody or other specific binding domain).

In certain aspects, the kit may also include one or more additional fluorescent compositions. The one or more additional fluorescent compositions may be provided in separate containers (e.g., separate tubes, bottles, or wells in a multi-well strip or plate).

In certain aspects, the kit may further include reagents for performing a flow cytometric assay. Examples of said reagents include buffers for at least one of reconstitution and dilution of the first and second detectible molecules, buffers for contacting a cell sample with one or both of the first and second detectible molecules, wash buffers, control cells, control beads, fluorescent beads for flow cytometer calibration and combinations thereof. The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The fluorescent composition may be provided in a liquid composition, such as any suitable buffer. Alternatively, the fluorescent composition may be provided in a dry composition (e.g., may be lyophilized), and the kit may optionally include one or more buffers for reconstituting the dry composition. In certain aspects, the kit may include aliquots of the fluorescent composition provided in separate containers (e.g., separate tubes, bottles, or wells in a multi-well strip or plate).

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

The following experiments demonstrate that when an environmentally sensitive dye is encapsulated in a heme-protein, the fluorescence of the dye is increased in an aqueous solution.

Apo-myoglobin (Apo-Mb) was examined as an encapsulation system for water insoluble and/or environmentally-sensitive fluorescent organic dyes. The utility of Apo-Mb was studied with and without the heme-coordinating histidine residues intact (e.g., H64 and H93 of human myoglobin, as seen in the molecular structure shown in FIG. 1). The protein was altered using recombinant techniques to maximize dye interactions while decreasing its affinity for the "heme" structure that naturally occurs in myoglobin. Histidine amino acid replacement included alanine, leucine, phenylalanine and tryptophan. In addition, amino acid residues above and below the edge of the heme-binding site were replaced with cysteines. These recombinant modifications were made for collapsing the cavity with a cysteine reactive bis-maleimide crosslinker post dye docking in the protein cavity. An alternate method for securing the dye was fixation using other standard chemical methods. Apo-Mb based encapsulation creates new fluorescent proteins without covalent attachment of a fluorophore. Post dye incorporation, the protein/dye monomer was externally cross-linked with 6 to 10 monomers creating a fluorescence enhancing system for the monomeric dye.

Figure 2:
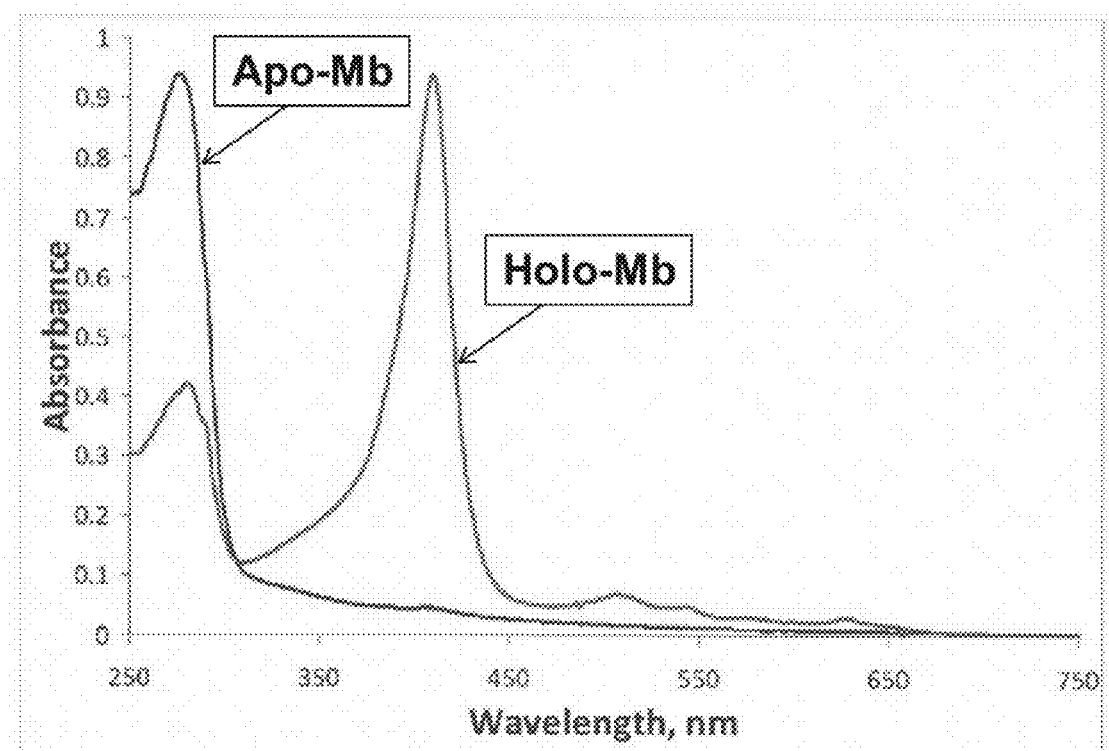
FIG. 2 provides a graph of the absorption spectrum of purified apo-myoglobin as compared to the absorption spectrum of holo-myoglobin.

The technical principle is to generate a generic protein encapsulation system utilizing the naturally occurring cavity in the myoglobin (FIG. 1) that is capable of associating with the "heme" structure in living organisms (FIG. 2). Replacing the heme with an environmentally sensitive dye such those in the squaraine family (FIG. 3) and collapsing the cavity generates a stable monomer that fluoresces in aqueous media (FIG. 4). The nature of the parent protein affords a non-polar environment and/or solubility to the organic dye. Once docked the cavity may be collapsed via sulfhydryl-maleimide chemistry and/or fixation via paraformaldehyde.

Expression and Purification of Ado-Mb and its Mutants

Human myoglobin was cloned from IMAGE clone 4244838 into the pVEXHN expression vector via HindIII/EcoRI restriction sites. Protein expression was induced in the BL21 strain of *E. coli* by adding 0.5 mM IPTG to a bacterial culture grown in M9 minimal medium to an OD600 of 0.8. After overnight incubation at room temperature the bacteria were pelleted and resuspended in 150 mM NaCl, 1 mM mercaptoethanol, 25 mM Na phosphate buffer, pH 7.4. Cells were sonified followed by 30 min centrifugation at 3000 g. Apo-Mb was purified on Ni-NTA agarose (QIAGEN) and eluted with 250 mM imidazole. The protein was further purified by size exclusion chromatography on Superdex 75 10/300 or HiLoad Superdex 7516/60 column in 150 mM NaCV25 mM Na phosphate buffer, pH 7.4. The resulting Apo-Mb is free from heme group and shows lack of light absorption at 409 nm, as seen if FIG. 2.

EXAMPLE 1

In Example 1, an encapsulation system for water insoluble and/or environmentally-sensitive fluorescent organic dyes was examined. The stability of such complexes was studied with and without the heme coordinating histidine residues of the protein intact. The protein was altered using recombinant techniques to maximize dye interactions while decreasing its affinity for the "heme" structure that naturally occurs in myoglobin. Histidine amino acid replacement included alanine, leucine, phenylalanine and tryptophan. In addition, amino acid residues above and below the edge of the heme binding site were replaced with cysteines. These recombinant modifications were made for locking the cavity with a cysteine reactive bis-maleimide (BS-3) crosslinker after binding the fluorescent organic molecule in the protein cavity. The binding affinity of the fluorescent molecule was measured against competition from a hemin molecule.

FIG. 7 shows the results of one such binding assay. Human recombinant apo-Mb was incubated with 2× excess of mono-squaraine in 50 mM sodium phosphate buffer, 150 mM sodium chloride, pH 7.2. Then, 0.5 ml samples of the apo-Mb/mono-squaraine complex containing 25 nmoles of apo-Mb were incubated for 2 hours with 175, 250 and 375 nmols of BS3 reagent (7, 10 and 15× crosslinker excess, respectively). The fluorescent signal of mono-squaraine-apo-myoglobin complex was measured as a function of increasing hemin concentration. They dye-protein complex was treated with three different concentration of crosslinking reagent bismaleimide (BS-3). It can be seen from the graph of FIG. 4 that crosslinked apo-myoglobin is significantly more resistant to displacement of the fluorophore by hemin than non-crosslinked apo-myoglobin. This beneficially provides for a stable fluorescent reagent that may be used in peripheral blood samples including free hemin.

EXAMPLE 2

The His64 and His93 amino acids of apo-myoglobin (apo-Mb) were genetically modified to form a modified apo-Mb with an improved affinity for mono- or bis-squaraines. Histidine amino acid replacement included alanine, leucine, phenylalanine and tryptophan. Shown below in Table 1 are binding constants for a variety of genetically modified apo-MB species, indicating that the affinity of mono- and bis-squaraine to apo-Mb may be modified by genetic modification of histidine residues in the protein.

TABLE 1

| | MonoSQ Kd (nM) | MonoSQ % from Kd ApoMb | BisSQ Kd (nM) | BisSQ % from Kd ApoMb |
|---|---|---|---|---|
| ApoMb (H64/H93) | 2.3 | 100 | 13.3 | 100 |
| A64 | 3.1 | 134.8 | 2 | 15 |
| L64 | 2.1 | 91.3 | 11.5 | 86.5 |
| F64 | 4.8 | 208.7 | 15.5 | 116.5 |
| W64 | 6.2 | 269.6 | 34.8 | 261.7 |
| A93 | 5.1 | 221.7 | 3.7 | 27.8 |
| L93 | 4.9 | 213 | 15.2 | 114.3 |
| F93 | 2.1 | 91.3 | 23.1 | 173.7 |
| W93 | 4.5 | 195.7 | 8.4 | 63.2 |

Through amino acid replacement the dye binding is optimized (FIG. 8). Amino acid SEQ ID NO:01 is shown in FIG. 8. Amino acids 3 to 14 of SEQ ID NO:01 are of a histidine tag enabling purification by Ni-NTA affinity. M27 of SEQ ID NO:01 corresponds to the initiator methionine of the wild-type human myoglobin sequence. Amino acids 28 to 180 correspond to a human myoglobin sequence of 153 amino acids with the following mutations: H64 of the wild-type sequence has been replaced with alanine (A91 of SEQ ID NO:01); H93 of the wild-type sequence has been replaced with phenylalanine (F120 of SEQ ID NO:01); and amino acid residues above and below the edge of the heme-binding site were replaced with cysteines (C94 and C119 of SEQ ID NO:01). In certain aspects, the amino acid sequence starting with M27 or G28 of SEQ ID NO:01 may be suitable for any embodiments of the invention described herein.

Notwithstanding the appended clauses, the disclosure is also defined by the following clauses:

1. A fluorescent composition, the composition comprising:
   a fluorescent component comprising:
   (i) a metalloprotein comprising a prosthetic group binding cavity; and
   (ii) a fluorescent dye moiety stably associated with the prosthetic group binding cavity;
   wherein the metalloprotein comprises a stabilizing modification that enhances association of the dye moiety with the cavity.
2. The composition according to Clause 1, wherein the prosthetic group binding cavity has a volume ranging from 50 nm³ to 1000 nm³.
3. The composition according to Clause 2, wherein the metalloprotein is a heme binding protein or mutant thereof.
4. The composition according to Clause 3, wherein the heme binding protein is an apo-myoglobin.
5. The composition according to Clause 4, wherein the apo-myoglobin has a wild-type sequence.
6. The composition according to Clause 4, wherein the apo-myoglobin includes one or more mutations.
7. The composition according to Clause 6, wherein the mutation is a point mutation.
8. The composition according to Clause 7, wherein the point mutation comprises a substitution of a cysteine residue for a naturally occurring amino acid residue.
9. The composition according to Clause 7, wherein the point mutation comprises a substitution of a non-histidine residue for a naturally occurring histidine residue.
10. The composition according to Clause 9, wherein the non-histidine residue is selected from the group consisting of alanine, leucine, phenylalanine, and tryptophan.
11. The composition according to any of the preceding clauses, wherein the fluorescent dye moiety comprises a non-protein organic fluorophore.
12. The composition according to Clause 11, wherein the organic fluorophore has a molecular weight ranging from 50 Da to 5 kDa.
13. The composition according to Clause 11, wherein the organic fluorophore is an environmentally sensitive fluorophore.
14. The composition according to Clause 13, wherein an environmentally sensitive fluorophore stably associated with the prosthetic group binding cavity of the metalloprotein has a first fluorescence intensity that is higher than a second fluorescence intensity of the environmentally sensitive fluorophore free in aqueous solution.
15. The method of Clause 14, wherein the first fluorescence intensity is at least 50 times higher than the second fluorescence intensity.
16. The composition according to Clause 13, wherein the environmentally sensitive fluorophore is a squaraine dye.
17. The composition according to any of the preceding clauses, wherein the fluorescent dye moiety is non-covalently bound to the prosthetic binding group cavity.
18. The composition according to any of the preceding clauses, wherein the composition further comprises a specific binding domain.
19. The composition according to Clause 18, wherein the specific binding domain has an affinity for an analyte of $K_A$ of $10^4$ M$^{-1}$ or greater.
20. The composition according to Clause 19, wherein the specific binding domain comprises a peptidic or polypeptidic moiety.
21. The composition according to Clause 20, wherein the peptidic or polypeptidic moiety comprises an antibody or binding fragment thereof.
22. The composition according to Clause 21, wherein the peptidic or polypeptidic moiety specifically binds a cell surface marker.
23. The composition according to Clause 18, wherein the specific binding domain is a ligand that specifically binds a cell surface receptor.
24. The composition according to Clause 18, wherein the specific binding domain comprises a nucleic acid moiety.
25. The composition according to any of the preceding clauses, further comprising a linker conjugated to the metalloprotein.
26. The composition according to any of the preceding clauses, wherein the composition comprises two or more fluorescent components covalently bound to each other.
27. The composition according to any of the preceding clauses, wherein the stabilizing modification comprises an internal crosslinking of the metalloprotein.
28. The composition according to Clause 27, wherein the internal crosslinking comprises crosslinked cysteine residues.
29. The composition according to Clause 27, wherein the internal crosslinking comprises crosslinked lysine residues.

30. A fluorescent composition, the composition comprising:
a fluorescent component comprising:
(i) a metalloprotein comprising a prosthetic group binding cavity; and
(ii) an environmentally sensitive fluorescent dye moiety stably associated with the prosthetic group binding cavity.

31. A method of assaying a sample, the method comprising:
contacting the sample with a fluorescent composition, wherein the fluorescent composition comprises:
i) a metalloprotein comprising a prosthetic group binding cavity;
ii) a fluorescent dye moiety stably associated with the prosthetic group binding cavity; and
wherein the metalloprotein comprises a stabilizing modification that enhances association of the dye moiety with the cavity.

32. The method according to Clause 31, wherein the fluorescent composition further comprises a specific binding domain.

33. The method according to Clause 32, further comprising obtaining a fluorescence signal from the sample.

34. The method according to Clause 33, further comprising evaluating an analyte based on the fluorescence signal.

35. The method according to Clause 34, wherein evaluating comprises assessing the amount of the analyte in the sample.

36. The method according to Clause 33, further comprising assessing the amount of a ligand as an inverse function of the intensity of the fluorescence signal, wherein the ligand competes for the analyte bound by the specific binding domain.

37. The method according to any of Clauses 31 to 36, wherein the biological sample is a cell sample.

38. The method according to any of Clauses 31 to 37, wherein the prosthetic group binding cavity has a volume ranging from 50 nm$^3$ to 1000 nm$^3$.

39. The method according to any of Clauses 31 to 38, wherein the metalloprotein is a heme binding protein or mutant thereof.

40. The method according to Clause 39, wherein the heme binding protein is an apo-myoglobin.

41. The method according to Clause 40, wherein the apo-myoglobin has a wild-type sequence.

42. The method according to Clause 40, wherein the apo-myoglobin includes one or more mutations.

43. The method according to Clause 42, wherein the mutation is a point mutation.

44. The method according to Clause 43, wherein the point mutation comprises a substitution of a cysteine for a naturally occurring amino acid residue.

45. The method according to Clause 44, wherein the point mutation comprises a substitution of a non-histidine residue for a naturally occurring histidine residue.

46. The method according to Clause 45, wherein the non-histidine residue is selected from the group consisting of alanine, leucine, phenylalanine, and tryptophan.

47. The method according to any of Clauses 31 to 46, wherein the fluorescent dye moiety comprises a non-protein organic fluorophore.

48. The method according to Clause 47, wherein the organic fluorophore has a molecular weight ranging from 50 Da to 5 kDa.

49. The method according to Clause 48, wherein the organic fluorophore is an environmentally sensitive fluorophore.

50. The method according to Clause 49, wherein an environmentally sensitive fluorophore stably associated with the prosthetic group binding cavity of the metalloprotein has a first fluorescence intensity that is higher than a second fluorescence intensity of the environmentally sensitive fluorophore free in aqueous solution.

51. The method according to Clause 50, wherein the first fluorescence intensity is at least 50 times higher than the second fluorescence intensity.

52. The method according to Clause 49 or 50, wherein the environmentally sensitive fluorophore is a squaraine dye.

53. The method according to any of Clauses 31 to 52, wherein the fluorescent dye moiety is non-covalently bound to the prosthetic binding group cavity.

54. The method according to any of Clauses 32 to 53, wherein the specific binding domain has an affinity for an analyte of $K_A$ of $10^4$ M$^{-1}$ or greater.

55. The method according to Clause 54, wherein the specific binding domain comprises a peptidic or polypeptidic moiety.

56. The method according to Clause 55, wherein the peptidic or polypeptidic moiety comprises an antibody or binding fragment thereof.

57. The method according to Clause 56, wherein the peptidic or polypeptidic moiety specifically binds a cell surface marker.

58. The method according to any of Clauses 32 to 53, wherein the specific binding domain is a ligand that specifically binds a cell surface receptor.

59. The method according to any of Clauses 32 to 53, wherein the specific binding domain comprises a nucleic acid moiety.

60. The method according to any of Clauses 31 59, wherein the fluorescent composition comprises two or more fluorescent compositions covalently bound to each other.

61. The method according to any of Clauses 31 to 60, wherein the stabilizing modification comprises an internal crosslinking of the metalloprotein.

62. The method according to Clause 61, wherein the internal crosslinking comprises crosslinking cysteine residues.

63. The method according to Clauses 61 or 62, wherein the internal crosslinking comprises crosslinking lysine residues.

64. A method of producing a fluorescent composition, the method comprising:
contacting a metalloprotein having an empty prosthetic group binding cavity with a fluorescent dye moiety in a manner sufficient for the fluorescent dye moiety to enter the prosthetic group binding cavity, and
stably associating the fluorescent dye moiety with the prosthetic group binding cavity.

65. The method according to Clause 64, wherein stably associating the fluorescent dye moiety with the prosthetic group binding cavity comprises modifying the metalloprotein.

66. The method according to Clause 65, wherein modifying the metalloprotein comprises generating an internal crosslink in the metalloprotein after the dye enters the prosthetic group binding cavity.

67. The method according to Clause 66, wherein a cysteine residue of the metalloprotein replaces a non-cysteine residue of a naturally occurring metalloprotein.

68. The method according to Clause 66, further comprising modulating pH prior to generating an internal crosslink in the metalloprotein.

69. The method according to any of Clauses 64 to 68, wherein the prosthetic group binding cavity has a volume ranging from 50 nm$^3$ to 1000 nm$^3$.

70. The method according to any of Clauses 64 to 69, wherein the metalloprotein is a heme binding protein or mutant thereof.
71. The method according to Clause 70, wherein the heme binding protein is an apo-myoglobin.
72. The method according to Clause 71, wherein the apo-myoglobin has a wild-type sequence.
73. The method according to Clause 71, wherein the apo-myoglobin includes one or more mutations.
74. The method according to Clause 73, wherein the mutation is a point mutation.
75. The method according to Clause 74, wherein the point mutation comprises a substitution of a cysteine for a naturally occurring amino acid residue.
76. The method according to Clause 74, wherein the point mutation comprises a substitution of a non-histidine residue for a naturally occurring histidine residue.
77. The method according to Clause 76, wherein the non-histidine residue is selected from the group consisting of alanine, leucine, phenylalanine, and tryptophan.
78. The method according to any of Clauses 64 to 77, wherein the fluorescent dye moiety comprises a non-protein organic fluorophore.
79. The method according to Clause 78, wherein the organic fluorophore has a molecular weight ranging from 50 Da to 5 kDa.
80. The method according to Clause 79, wherein the organic fluorophore is an environmentally sensitive fluorophore.
81. The method according to Clause 80, wherein an environmentally sensitive fluorophore stably associated with the prosthetic group binding cavity of the metalloprotein has a first fluorescence intensity that is higher than a second fluorescence intensity of the environmentally sensitive fluorophore free in aqueous solution.
82. The method according to Clause 81, wherein the first fluorescence intensity is at least 50 times higher than the second fluorescence intensity.
83. The method according to Clauses 80, 81 or 82, wherein the environmentally sensitive fluorophore is a squaraine dye.
84. The method according to any of Clauses 64 to 83, wherein the fluorescent dye moiety is non-covalently bound to the prosthetic binding group cavity.
85. The method according to any of Clauses 64 to 84, wherein the fluorescent composition further comprises a specific binding domain.
86. The method according to Clause 85, wherein the specific binding domain has an affinity for an analyte of $K_A$ of $10^4$ $M^{-1}$ or greater.
87. The method according to Clause 86, wherein the specific binding domain comprises a peptidic or polypeptidic moiety.
88. The method according to Clause 87, wherein the peptidic or polypeptidic moiety comprises an antibody or binding fragment thereof.
89. The method according to Clause 88, wherein the peptidic or polypeptidic moiety specifically binds a cell surface marker.
90. The method according to Clause 85, wherein the specific binding domain is a ligand that specifically binds a cell surface receptor.
91. The method according to Clause 85, wherein the specific binding domain comprises a nucleic acid moiety.
92. The method according to any of Clauses 64 to 91, wherein the fluorescent composition comprises two or more fluorescent compositions covalently bound to each other.
93. A method of producing a metalloprotein suitable for binding to a fluorescent dye moiety, the method comprising:
expressing a mutant metalloprotein in a host cell, wherein the mutant metalloprotein comprises a mutation in a prosthetic group binding cavity; and
harvesting the mutant metalloprotein from the host cell.
94. The method according to Clause 93, wherein the prosthetic group binding cavity has a volume ranging from 50 $nm^3$ to 1000 $nm^3$.
95. The method according to Clause 94, wherein the metalloprotein is a heme binding protein.
96. The method according to Clause 95, wherein the heme binding protein is an apo-myoglobin.
97. The method according to Clause 96, wherein the apo-myoglobin includes one or more mutations.
98. The method according to Clause 97, wherein the mutations comprise at least one of a substitution, point mutation, insertion, and a deletion.
99. The method according to Clause 97, wherein the mutation is a point mutation.
100. The method according to Clause 99, wherein the point mutation comprises a substitution of a cysteine for a naturally occurring amino acid residue.
101. The method according to Clause 99, wherein the point mutation comprises a substitution of a non-histidine residue for a naturally occurring histidine residue.
102. The method according to Clause 101, wherein the non-histidine residue is selected from the group consisting of alanine, leucine, phenylalanine, and tryptophan.
103. The method according to any of Clauses 93 to 102, wherein the host cell is of a bacterial strain.
104. The method according to any of Clauses 93 to 103, wherein the host cell is an animal cell.
105. The method according to Clause 104, wherein the animal cell is of a yeast strain.
106. The method according to any of Clauses 93 to 105, wherein expressing comprises exposing the host cell to a vector comprising a nucleotide sequence encoding the mutant metalloprotein.
107. The method according to Claim 106, wherein the method further comprises maintaining the exposed host cell under conditions sufficient for the nucleotide sequence to be expressed.
108. The method according to Clauses 106 or 107, wherein the vector is a virus.
109. The method according to Clauses 106 or 107, wherein the vector is a plasmid.
110. The method according to any of Clauses 106 to 109, wherein the nucleotide sequence is under the control of a promoter.
111. The method according to Clause 110, wherein the expression is inducible.
112. The method according to Clause 111, further comprising exposing the host cell to an inducing agent.
113. A kit comprising:
a fluorescent composition, the fluorescent composition comprising:
(i) a metalloprotein comprising a prosthetic group binding cavity; and
(ii) a fluorescent dye moiety stably associated with the prosthetic group binding cavity;
wherein the metalloprotein comprises a stabilizing modification that enhances association of the dye moiety with the cavity; and
a container comprising the fluorescent composition.

114. The kit according to Clause 113, wherein the stabilizing modification comprises an internal crosslinking of the metalloprotein.
115. The kit according to Clause 114, wherein the internal crosslinking comprises crosslinked cysteine residues.
116. The kit according to Clause 114, wherein the internal crosslinking comprises crosslinked lysine residues.
117. The kit according to any of Clauses 113 to 116, wherein the prosthetic group binding cavity has a volume ranging from 50 nm$^3$ to 1000 nm$^3$.
118. The kit according to any of Clauses 113 to 117, wherein the metalloprotein is a heme binding protein or mutant thereof.
119. The kit according to Clause 118, wherein the heme binding protein is an apo-myoglobin.
120. The kit according to Clause 119, wherein the apo-myoglobin has a wild-type sequence.
121. The kit according to Clause 120, wherein the apo-myoglobin includes one or more mutations.
122. The kit according to Clause 121, wherein the mutation is a point mutation.
123. The kit according to Clause 122, wherein the point mutation comprises a substitution of a cysteine for a naturally occurring amino acid residue.
124. The kit according to Clause 122, wherein the point mutation comprises a substitution of a non-histidine residue for a naturally occurring histidine residue.
125. The kit according to Clause 124, wherein the non-histidine residue is selected from the group consisting of alanine, leucine, phenylalanine, and tryptophan.
126. The kit according to any of Clauses 113 to 125, wherein the fluorescent dye moiety comprises a non-protein organic fluorophore.
127. The kit according to Clause 126, wherein the organic fluorophore has a molecular weight ranging from 50 Da to 5 kDa.
128. The kit according to Clause 127, wherein the organic fluorophore is an environmentally sensitive fluorophore.
129. The kit according to Clause 128, wherein an environmentally sensitive fluorophore stably associated with the prosthetic group binding cavity of the metalloprotein has a first fluorescence intensity that is higher than a second fluorescence intensity of the environmentally sensitive fluorophore free in aqueous solution.
130. The kit according to Clause 129, wherein the first fluorescence intensity is at least 50 times higher than the second fluorescence intensity.
131. The kit according to Clause 128, wherein the environmentally sensitive fluorophore is a squaraine dye.
132. The kit according to any of Clauses 113 to 131, wherein the fluorescent dye moiety is non-covalently bound to the prosthetic binding group cavity.
133. The kit according to any of Clauses 113 to 132, wherein the fluorescent composition further comprises a specific binding domain.
134. The kit according to Clause 133, wherein the specific binding domain has an affinity for an analyte of $K_A$ of $10^4$ M$^{-1}$ or greater.
135. The kit according to Clause 134, wherein the specific binding domain comprises a peptidic or polypeptidic moiety.
136. The kit according to Clause 135, wherein the peptidic or polypeptidic moiety comprises an antibody or binding fragment thereof.
137. The kit according to Clause 136, wherein the peptidic or polypeptidic moiety specifically binds a cell surface marker.
138. The kit according to Clause 133, wherein the specific binding domain is a ligand that specifically binds a cell surface receptor.
139. The kit according to Clause 133, wherein the specific binding domain comprises a nucleic acid moiety.
140. The kit according to any of Clauses 113 to 139, wherein the fluorescent composition further comprises a linker conjugated to the metalloprotein.
141. The kit according to any of Clauses 113 to 140, wherein the fluorescent composition comprises two or more fluorescent compositions covalently bound to each other.
142. The kit according to any of Clauses 113 to 141, further comprising reagents for performing a flow cytometric assay.
143. The kit according to any of Clauses 113 to 142, further comprising one or more additional fluorescent compositions.
144. The kit according to any of Clauses 113 to 143, wherein the fluorescent composition is in a liquid composition.
145. The kit according to any of Clauses 113 to 143, wherein the fluorescent composition is in a dry composition.
146. A sample analysis system comprising:
  a flow channel loaded with a sample comprising a fluorescent composition;
  wherein the fluorescent composition comprises:
    (i) a metalloprotein comprising a prosthetic group binding cavity; and
    (ii) a fluorescent dye moiety stably associated with the prosthetic group binding cavity.
147. The system according to Clause 146, further comprising a light source configured to direct light to an assay region of the flow channel.
148. The system according to Clause 147, further comprising a detector configured to receive a signal from an assay region of the flow channel, wherein the signal is provided by the fluorescent composition.
149. The system according to any of Clauses 146 to 148, wherein the metalloprotein comprises a stabilizing modification that enhances association of the dye moiety with the cavity.
150. The system according to Clause 149, wherein the stabilizing modification comprises an internal crosslinking of the metalloprotein.
151. The system according to Clause 150, wherein the internal crosslinking comprises crosslinked cysteine residues.
152. The system according to Clause 151, wherein the internal crosslinking comprises crosslinked lysine residues.
153. The system according to any of Clauses 146 to 152, wherein the prosthetic group binding cavity has a volume ranging from 50 nm$^3$ to 1000 nm$^3$.
154. The system according to any of Clauses 146 to 153, wherein the metalloprotein is a heme binding protein or mutant thereof.
155. The system according to Clause 154, wherein the heme binding protein is an apo-myoglobin.
156. The system according to Clause 155, wherein the apo-myoglobin has a wild-type sequence.
157. The system according to Clause 155, wherein the apo-myoglobin includes one or more mutations.
158. The system according to Clause 157, wherein the mutation is a point mutation.
159. The system according to Clause 158, wherein the point mutation comprises a substitution of a cysteine for a naturally occurring amino acid residue.

160. The system according to Clause 158, wherein the point mutation comprises a substitution of a non-histidine residue for a naturally occurring histidine residue.
161. The system according to Clause 160, wherein the non-histidine residue is selected from the group consisting of alanine, leucine, phenylalanine, and tryptophan.
162. The system according to any of Clauses 146 to 161, wherein the fluorescent dye moiety comprises a non-protein organic fluorophore.
163. The system according to Clause 162, wherein the organic fluorophore has a molecular weight ranging from 50 Da to 5 kDa.
164. The system according to Clause 163, wherein the organic fluorophore is an environmentally sensitive fluorophore.
165. The system according to Clause 164, wherein an environmentally sensitive fluorophore stably associated with the prosthetic group binding cavity of the metalloprotein has a first fluorescence intensity that is higher than a second fluorescence intensity of the environmentally sensitive fluorophore free in aqueous solution.
166. The system according to Clause 165, wherein the first fluorescence intensity is at least 50 times higher than the second fluorescence intensity.
167. The system according to Clause 164, wherein the environmentally sensitive fluorophore is a squaraine dye.
168. The system according to any of Clauses 146 to 167, wherein the fluorescent dye moiety is non-covalently bound to the prosthetic binding group cavity.
169. The system according to any of Clause 146 to 168, wherein the fluorescent composition further comprises a specific binding domain.
170. The system according to Clause 169, wherein the specific binding domain has an affinity for an analyte of $K_A$ of $10^4$ $M^{-1}$ or greater.
171. The system according to Clause 169, wherein the specific binding domain comprises a peptidic or polypeptidic moiety.
172. The system according to Clause 171, wherein the peptidic or polypeptidic moiety comprises an antibody or binding fragment thereof.
173. The system according to Clause 172, wherein the peptidic or polypeptidic moiety specifically binds a cell surface marker.
174. The system according to Clause 169, wherein the specific binding domain is a ligand that specifically binds a cell surface receptor.
175. The system according to Clause 169, wherein the specific binding domain comprises a nucleic acid moiety.
176. The system according to any of Clauses 146 to 175, wherein the fluorescent composition comprises two or more fluorescent compositions covalently bound to each other.
177. The system according to any of Clauses 146 to 176, wherein the sample comprises one or more additional fluorescent compositions.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of assaying for an analyte in a sample, the method comprising:
   contacting the sample with a fluorescent composition, wherein the fluorescent composition comprises:
   i) a metalloprotein comprising a prosthetic group binding cavity;
   ii) a fluorescent dye moiety stably associated with the prosthetic group binding cavity; and wherein the metalloprotein comprises an internal crosslink that enhances association of the dye moiety with the cavity, and
   iii) a binding domain that is specific for said analyte,
   assaying for a fluorescence signal from the sample,
   wherein the fluorescent signal indicates the presence of the analyte in said sample.

2. The method according to claim 1, wherein the amount of the analyte in the sample is determined.

3. The method according to claim 1, wherein the prosthetic group binding cavity has a volume ranging from 50 nm3 to 1000 nm3.

4. The method according to claim 1, wherein the metalloprotein is a heme binding protein or mutant thereof.

5. The method according to claim 4, wherein the heme binding protein is an apo-myoglobin or mutant thereof.

6. The method according to claim 5, wherein the apo-myogiobin has a wild-type sequence.

7. The method according to claim 5, wherein the apo-myoglobin includes a mutation.

8. The method according to claim 7, wherein the mutation comprises a substitution of a cysteine for a naturally occurring amino acid residue or a substitution of a non-histidine residue for a naturally occurring histidine residue.

9. The method according to claim 1, wherein the fluorescent dye moiety comprises a non-protein organic fluorophore.

10. The method according to claim 9, wherein the organic fluorophore has a molecular weight ranging from 50 Da to 5 kDa.

11. The method according to claim 10, wherein the organic fluorophore is an environmentally sensitive fluorophore.

12. The method according to claim 11, wherein the environmentally sensitive fluorophore is a squaraine dye.

13. The method according to claim 1, wherein the fluorescent dye moiety is non-covalently bound to the prosthetic binding group cavity.

14. The method according to claim 1, wherein the binding domain comprises an antibody or binding fragment thereof.

15. The method according to claim 1, wherein the method comprises flow cytometrically assaying the fluorescent composition contacted sample.

* * * * *

SEQUENCE LISTING

```
<160> NUMBER OF SEQ ID NOS: 1

<210> SEQ ID NO 1
<211> LENGTH: 180
<212> TYPE: PRT
<213> ORGANISM: Artificial sequence
<220> FEATURE:
<223> OTHER INFORMATION: Synthetic amino acid sequences

<400> SEQUENCE: 1

Met Gly His Asn His Asn His Asn His Asn His Asn Gly Gly
1               5                   10                  15

Asp Asp Asp Asp Lys Gly Ser Thr Ser Phe Met Gly Leu Ser Asp Gly
            20                  25                  30

Glu Trp Gln Leu Val Leu Asn Val Trp Gly Lys Val Glu Ala Asp Ile
        35                  40                  45

Pro Gly His Gly Gln Glu Val Leu Ile Arg Leu Phe Lys Gly His Pro
    50                  55                  60
```

```
Glu Thr Leu Glu Lys Phe Asp Lys Phe Lys His Leu Lys Ser Glu Asp
65                  70              75              80
Glu Met Lys Ala Ser Glu Asp Leu Lys Lys Ala Gly Ala Cys Val Leu
                85              90              95
Thr Ala Leu Gly Gly Ile Leu Lys Lys Lys Gly His His Glu Ala Glu
            100             105             110
Ile Lys Pro Leu Ala Gln Cys Phe Ala Thr Lys His Lys Ile Pro Val
        115             120             125
Lys Tyr Leu Glu Phe Ile Ser Glu Cys Ile Ile Gln Val Leu Gln Ser
    130             135             140
Lys His Pro Gly Asp Phe Gly Ala Asp Ala Gln Gly Ala Met Asn Lys
145             150             155             160
Ala Leu Glu Leu Phe Arg Lys Asp Met Ala Ser Asn Tyr Lys Glu Leu
            165             170             175
Gly Phe Gln Gly
            180
```